United States Patent
Lonski et al.

(10) Patent No.: US 6,338,039 B1
(45) Date of Patent: Jan. 8, 2002

(54) METHOD FOR AUTOMATED COLLECTION OF PSYCHOTHERAPY PATIENT INFORMATION AND GENERATING REPORTS AND TREATMENT PLANS

(75) Inventors: Michael Lonski, 112 Shore Rd., Old Greenwich, CT (US) 06870; Phil Burke, Wanaque, NJ (US)

(73) Assignee: Michael Lonski, Old Greenwich, CT (US)

(*) Notice: Subject to any disclaimer, the term of this patent is extended or adjusted under 35 U.S.C. 154(b) by 0 days.

(21) Appl. No.: 09/358,168

(22) Filed: Jul. 20, 1999

(51) Int. Cl.[7] .............................................. G06F 159/00
(52) U.S. Cl. ............................................ 705/3; 705/2
(58) Field of Search ............................................. 705/3

(56) References Cited

U.S. PATENT DOCUMENTS

| | | | |
|---|---|---|---|
| 5,099,424 A | * 3/1992 | Schneiderman et al. | 705/3 |
| 5,325,294 A | * 6/1994 | Keene | 705/3 |
| 5,327,341 A | 7/1994 | Whalen et al. | |
| 5,361,202 A | 11/1994 | Doue | |
| 5,435,324 A | 7/1995 | Brill | |
| 5,508,912 A | 4/1996 | Schneiderman | |
| 5,544,044 A | 8/1996 | Leatherman | |
| 5,592,945 A | 1/1997 | Fiedler | |
| 5,640,549 A | 6/1997 | Powsner et al. | |
| 5,711,297 A | 1/1998 | Iliff | |
| 5,724,580 A | 3/1998 | Levin et al. | |
| 5,732,221 A | 3/1998 | Feldon et al. | |
| 5,752,235 A | * 5/1998 | Kehr et al. | 705/3 |
| 5,764,923 A | * 6/1998 | Tallman et al. | 705/3 |
| 5,832,450 A | 11/1998 | Myers et al. | |
| 5,835,897 A | 11/1998 | Dang | |
| 5,842,175 A | * 11/1998 | Andros et al. | 705/3 |
| 5,845,253 A | * 12/1998 | Rensimer et al. | 705/2 |
| 5,845,254 A | 12/1998 | Lockwood et al. | |
| 5,913,197 A | * 6/1999 | Kameda | 705/3 |
| 5,991,729 A | * 11/1999 | Barry et al. | 705/3 |
| 6,026,363 A | * 2/2000 | Shepard | 705/3 |
| 6,047,259 A | * 4/2000 | Campbell et al. | 705/3 |
| 6,067,523 A | * 5/2000 | Bair et al. | 705/3 |

FOREIGN PATENT DOCUMENTS

| | | | | |
|---|---|---|---|---|
| EP | 0710490 A2 | * | 8/1996 | A61M/25/10 |

OTHER PUBLICATIONS

Mackarguhar L "Pint Duck—Sotware for Shrink" DNew Republic V214–N15 p 14(3).*
"Therapy on a Disk:The Computerized Road to Mental Health" Business Week–Aug. 19, 1985 p. 75.*
"Product Spotlight"–Behavioral Health Management 17, 1, 37 Jan. 1997.*

* cited by examiner

Primary Examiner—Vincent Millin
Assistant Examiner—Geoffrey Akers
(74) Attorney, Agent, or Firm—Pitney, Hardin, Kipp & Szuch LLP

(57) ABSTRACT

The method and apparatus automatedly generates various reports for a psychotherapy provider. These reports include Treatment Plans, progress reports, scheduling reports and billing reports. The progress reports include a Progress Note which incorporates various selected data into a report for the insurance company. As much of the data is selected from menus, the resulting report can maintain much patient privacy while being satisfactory to the insurance company. More private information can be stored separately in Expanded Text. A Treatment Plan is generated using the various selected data with respect to subsets of emotional factors, intellectual factors, physical factors, social factors, and spiritual factors. These subsets may be chosen randomly or with some periodic selection.

36 Claims, 21 Drawing Sheets

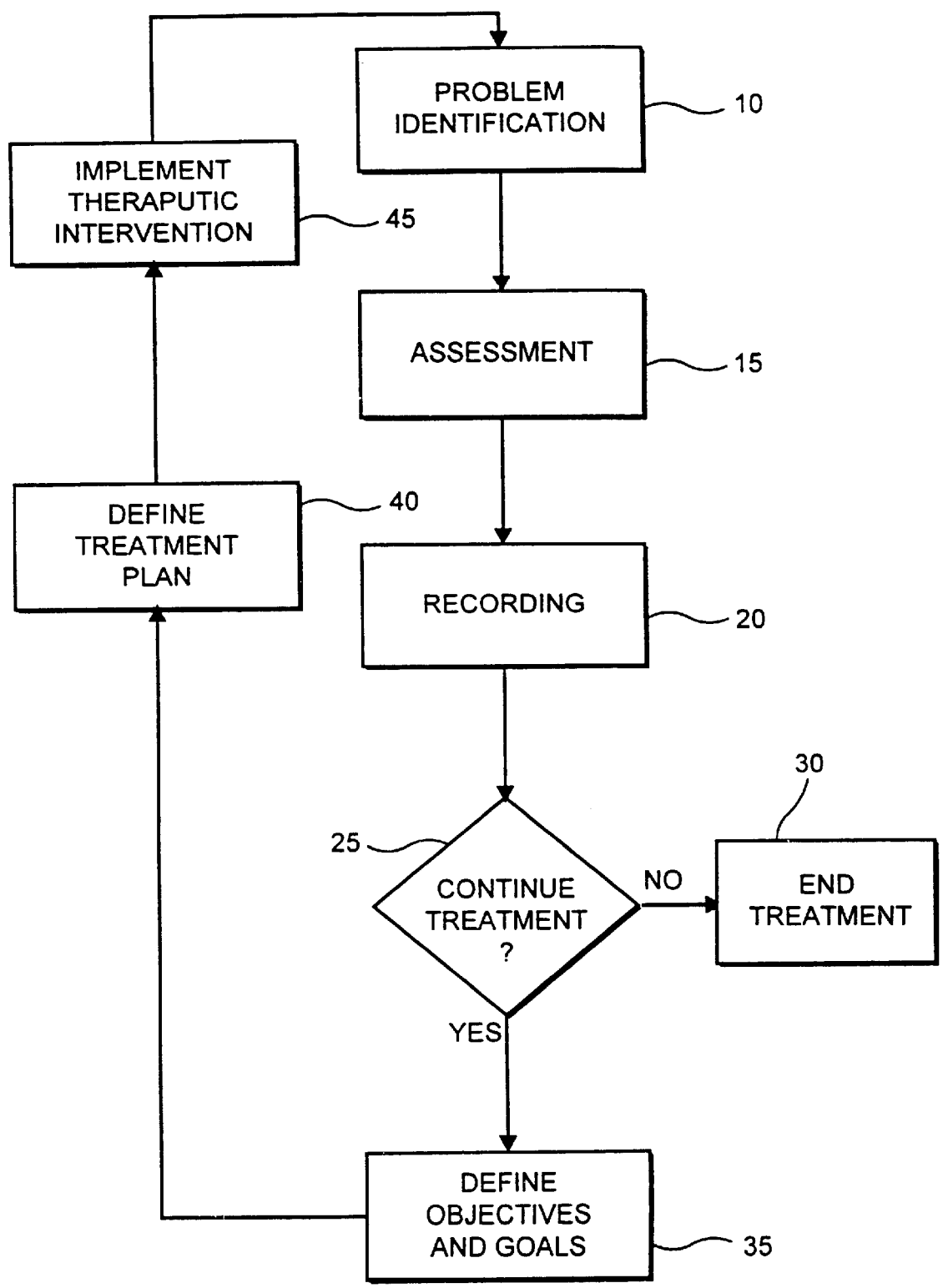
F I G. 1

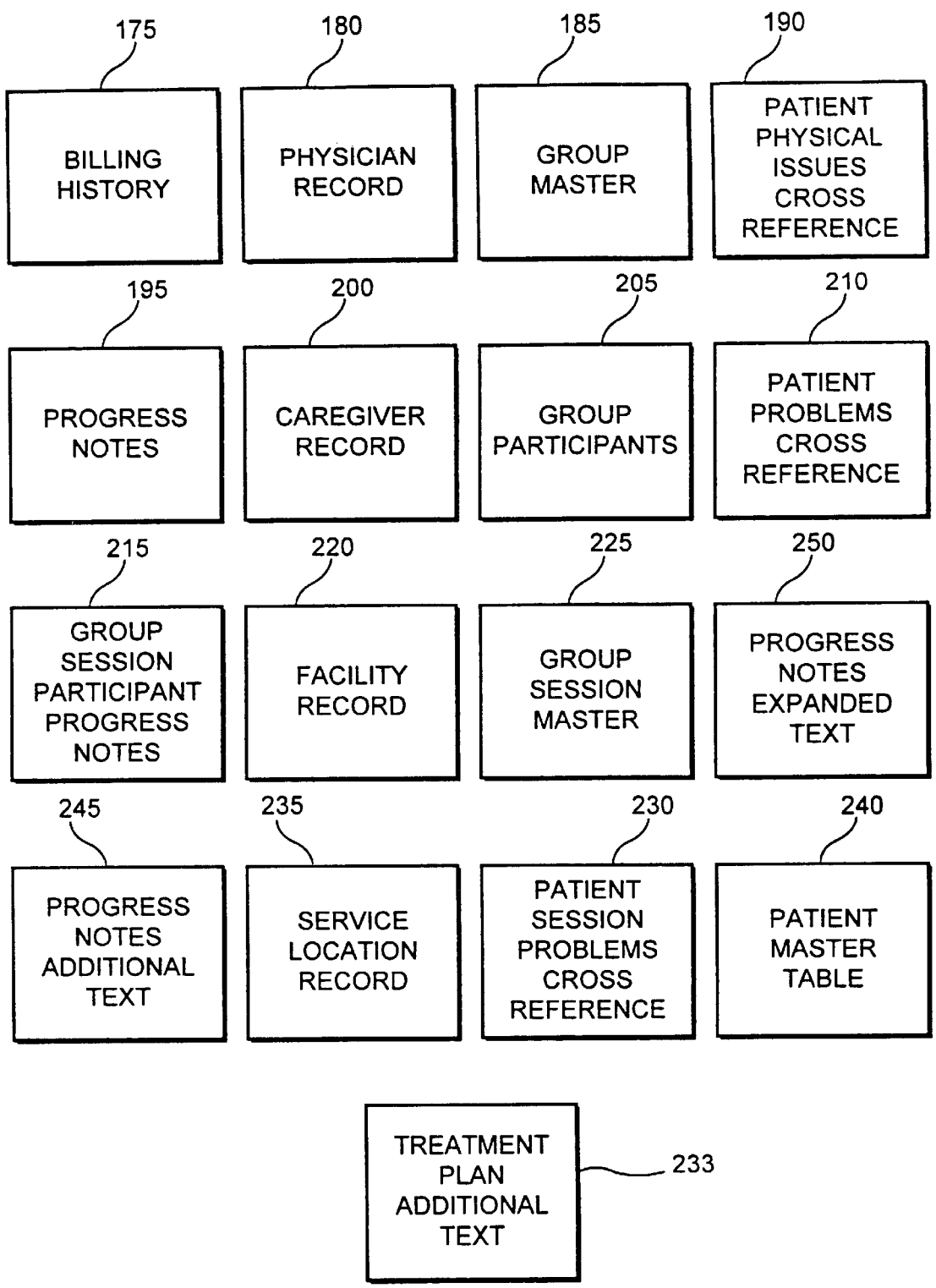
F I G. 4

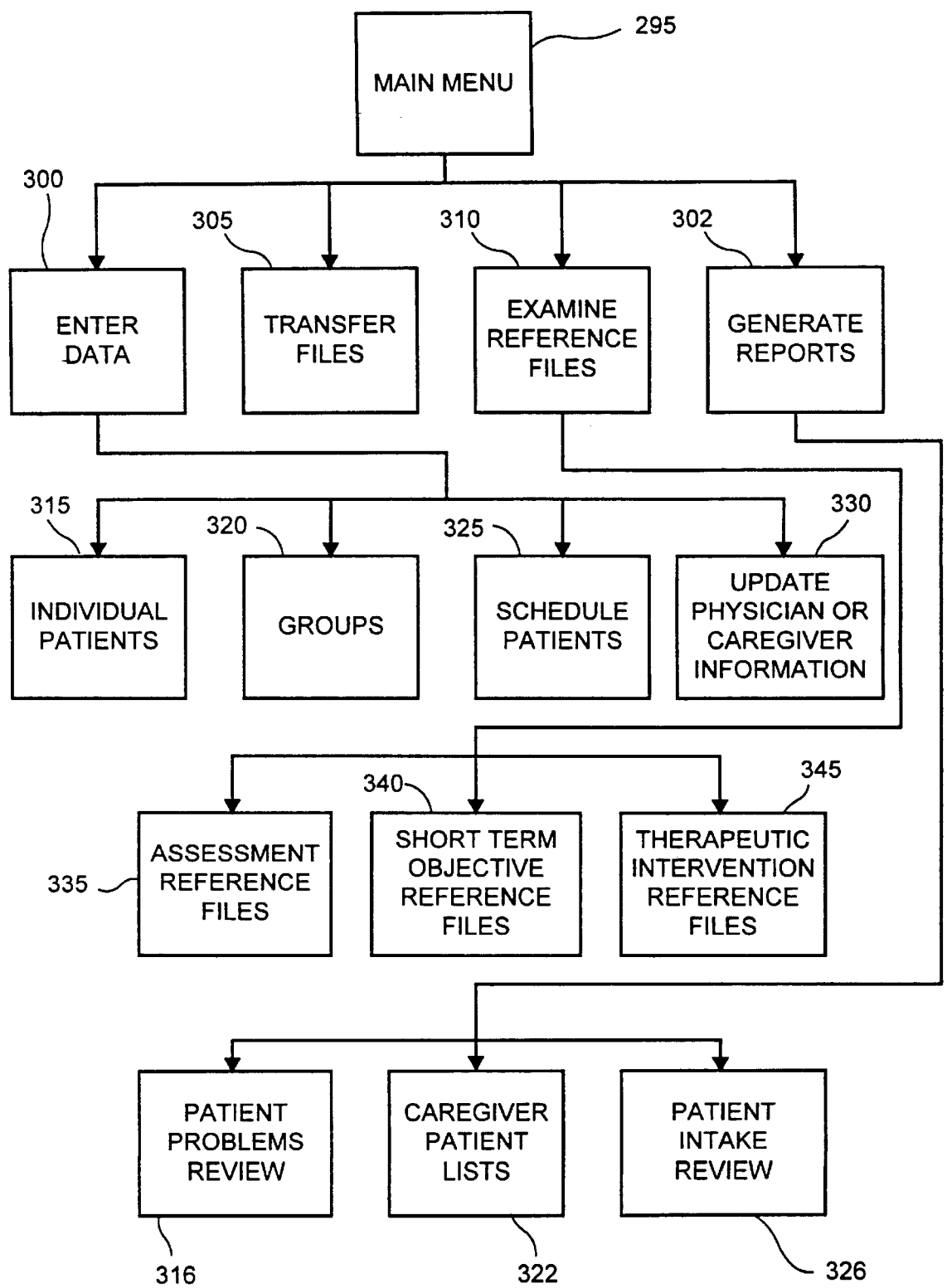
F I G. 6

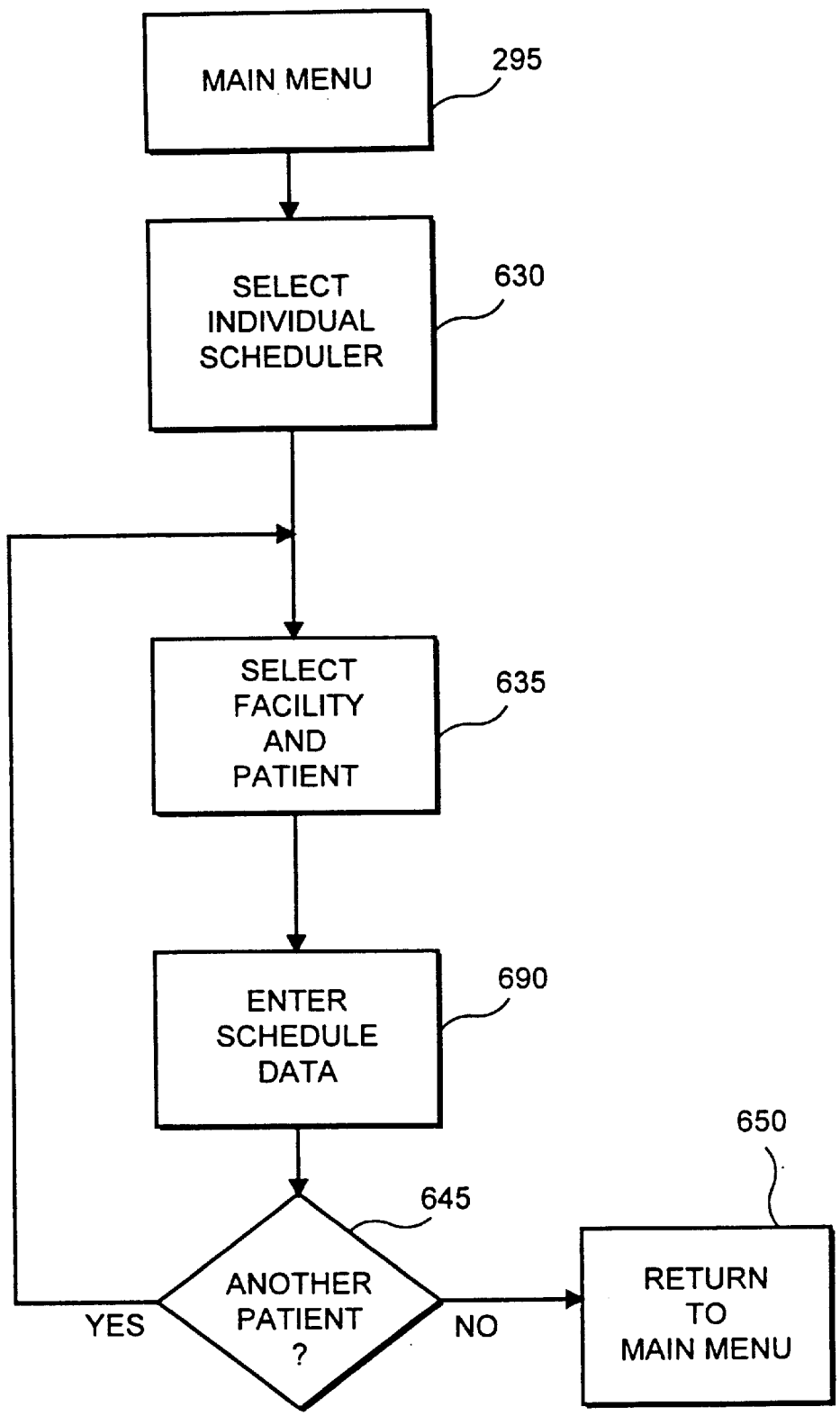
F I G. 10

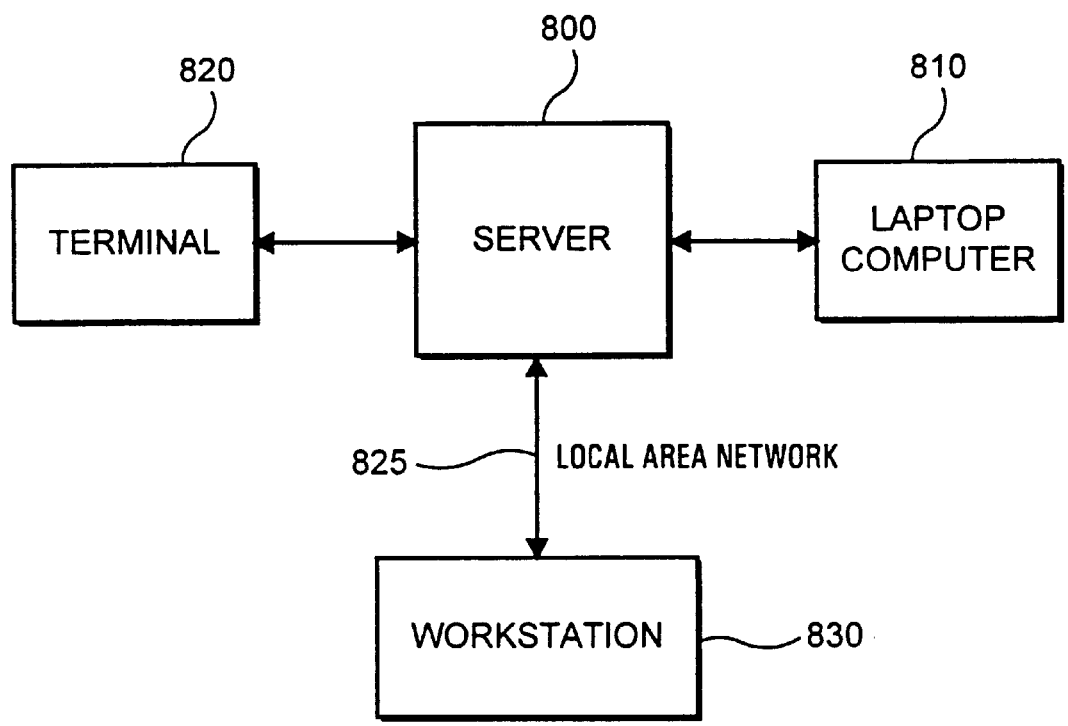
F I G. 13

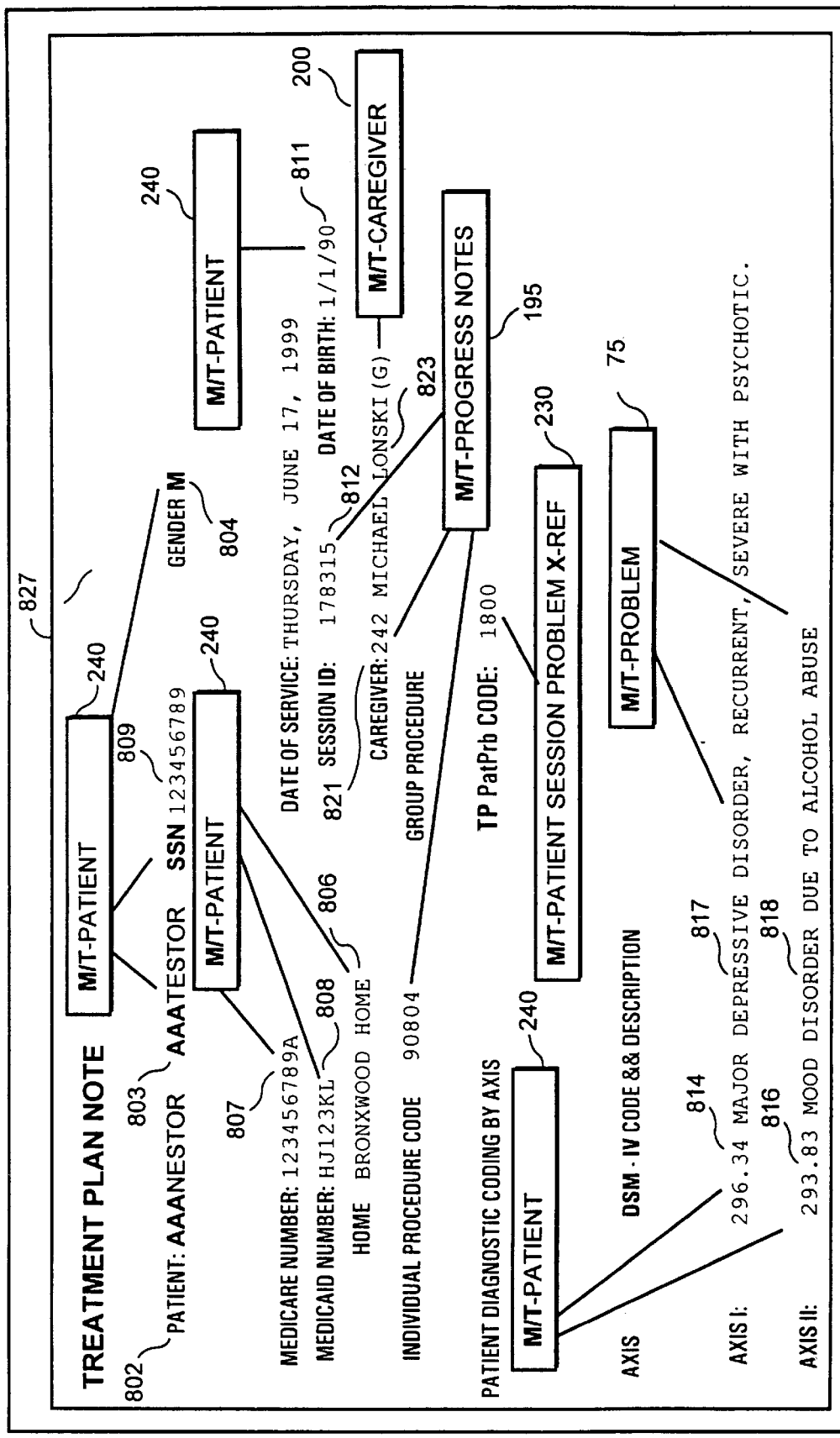
FIG. 14A1

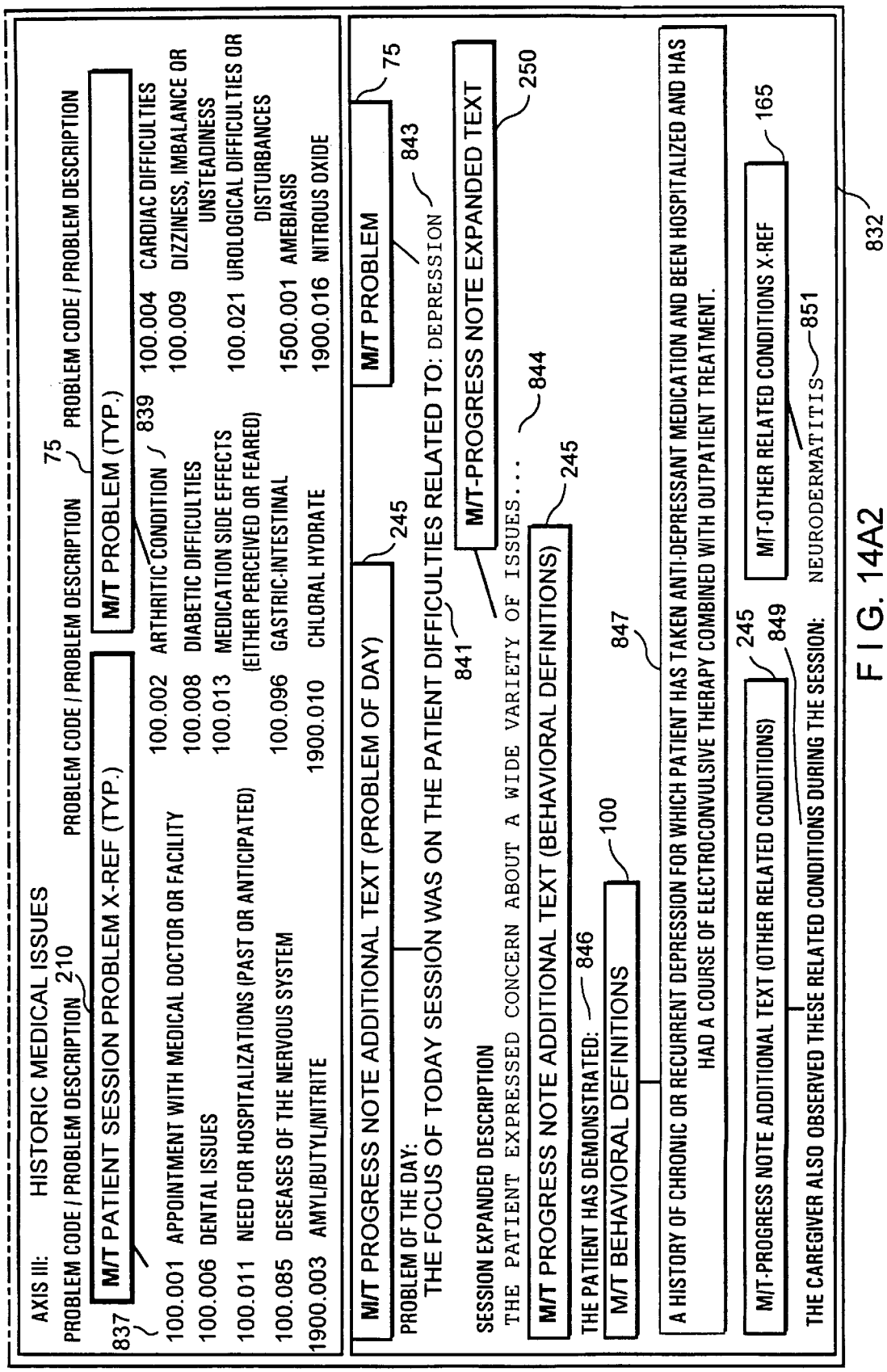

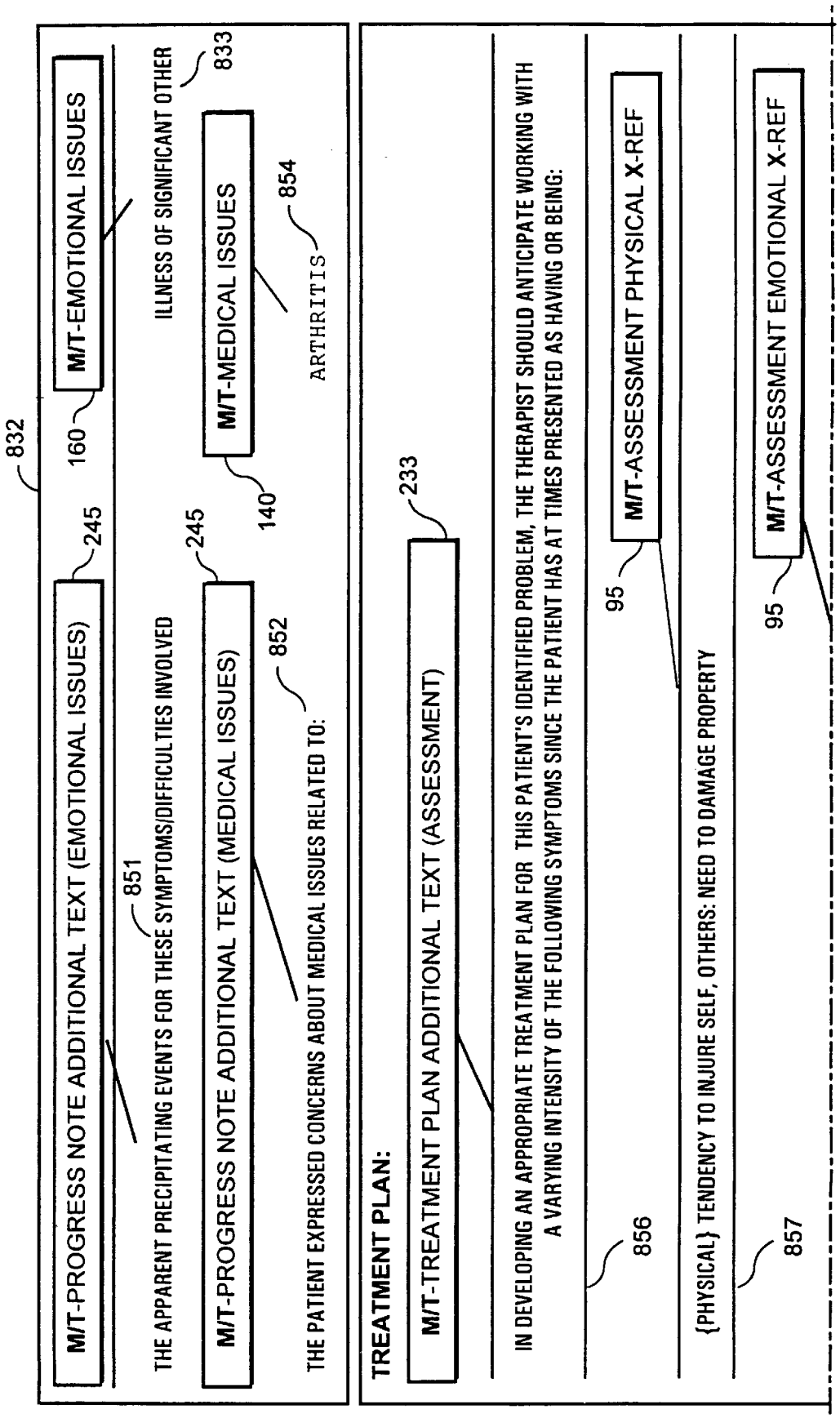
FIG. 14B1

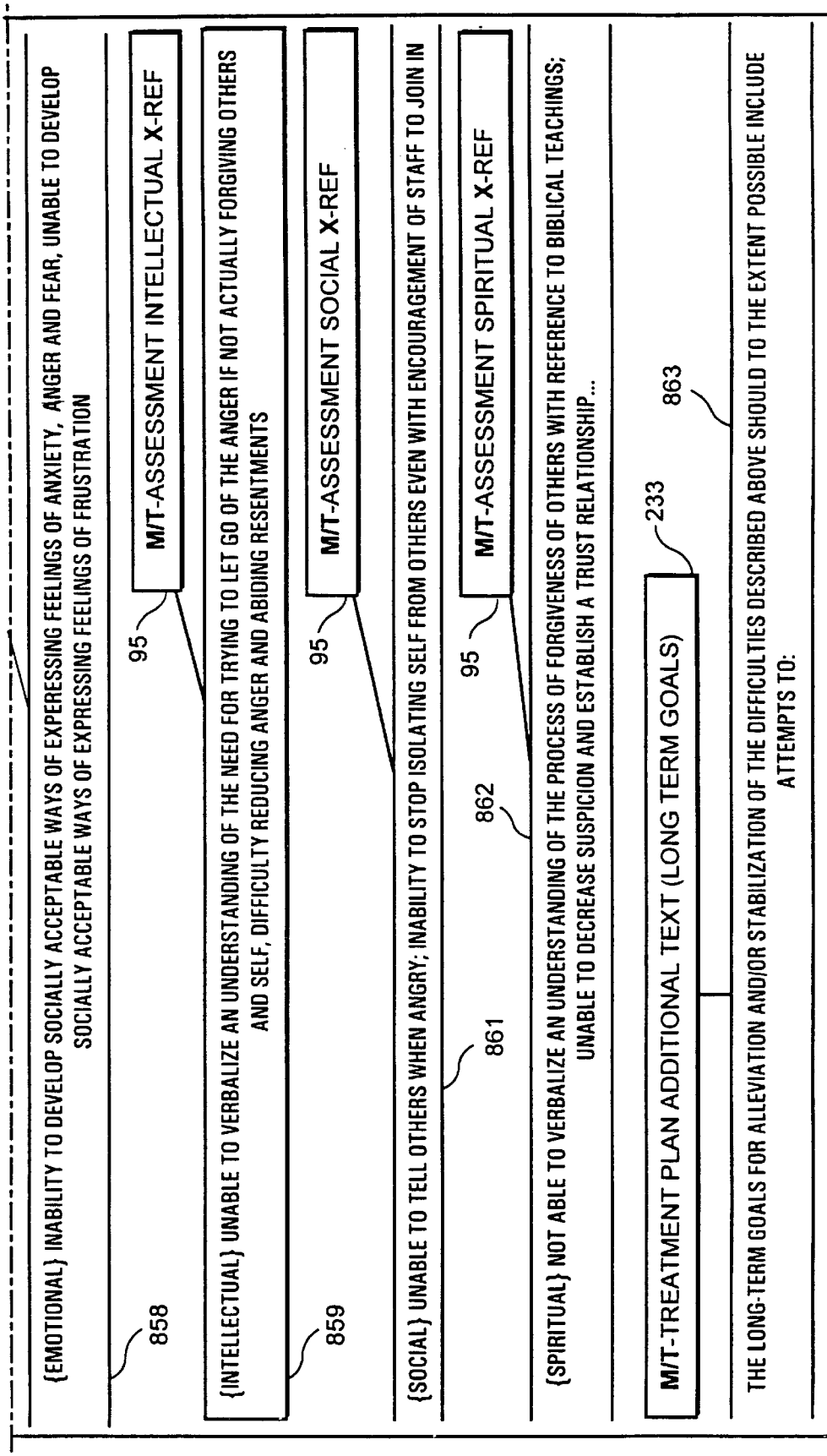
FIG. 14B2

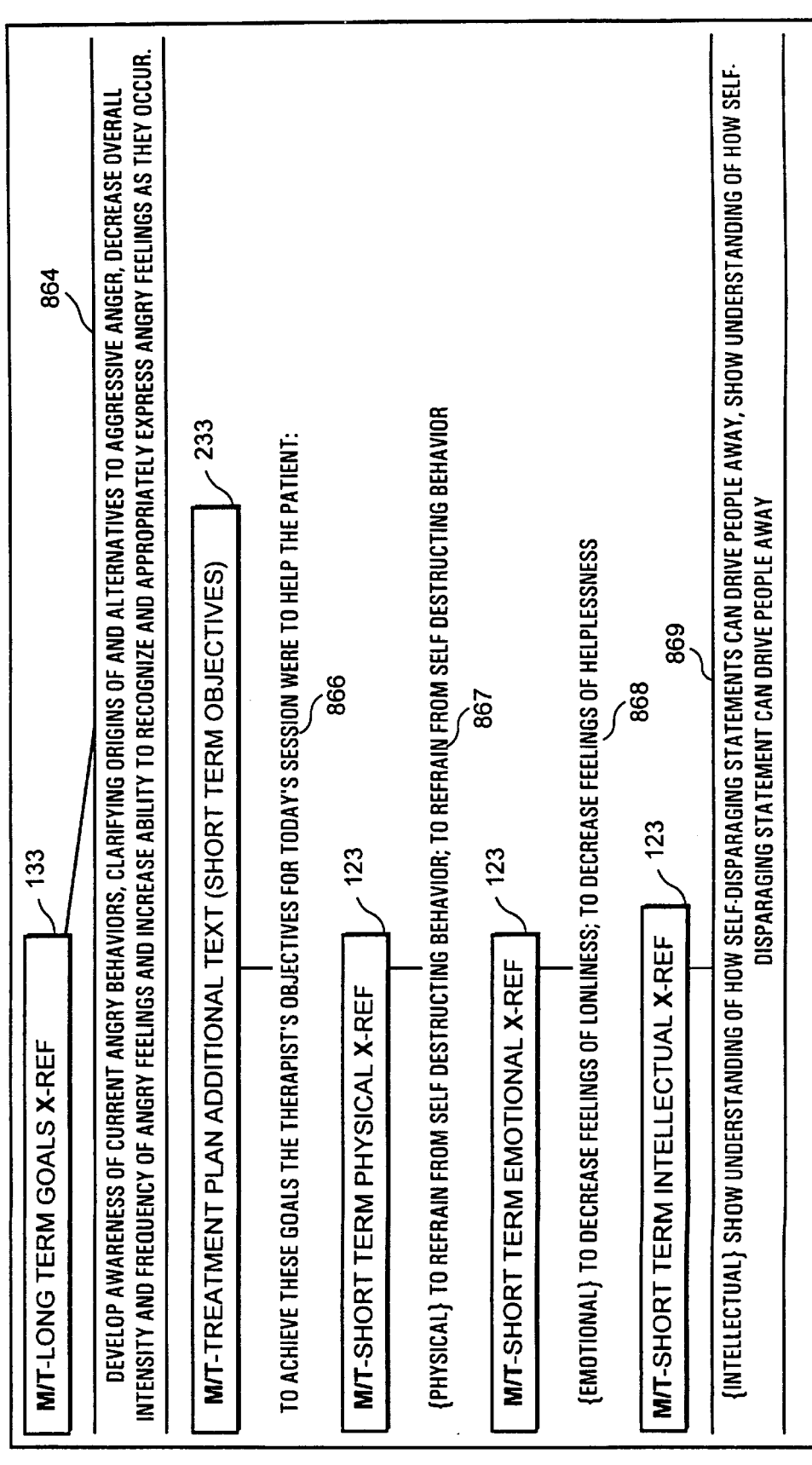
FIG. 14C1

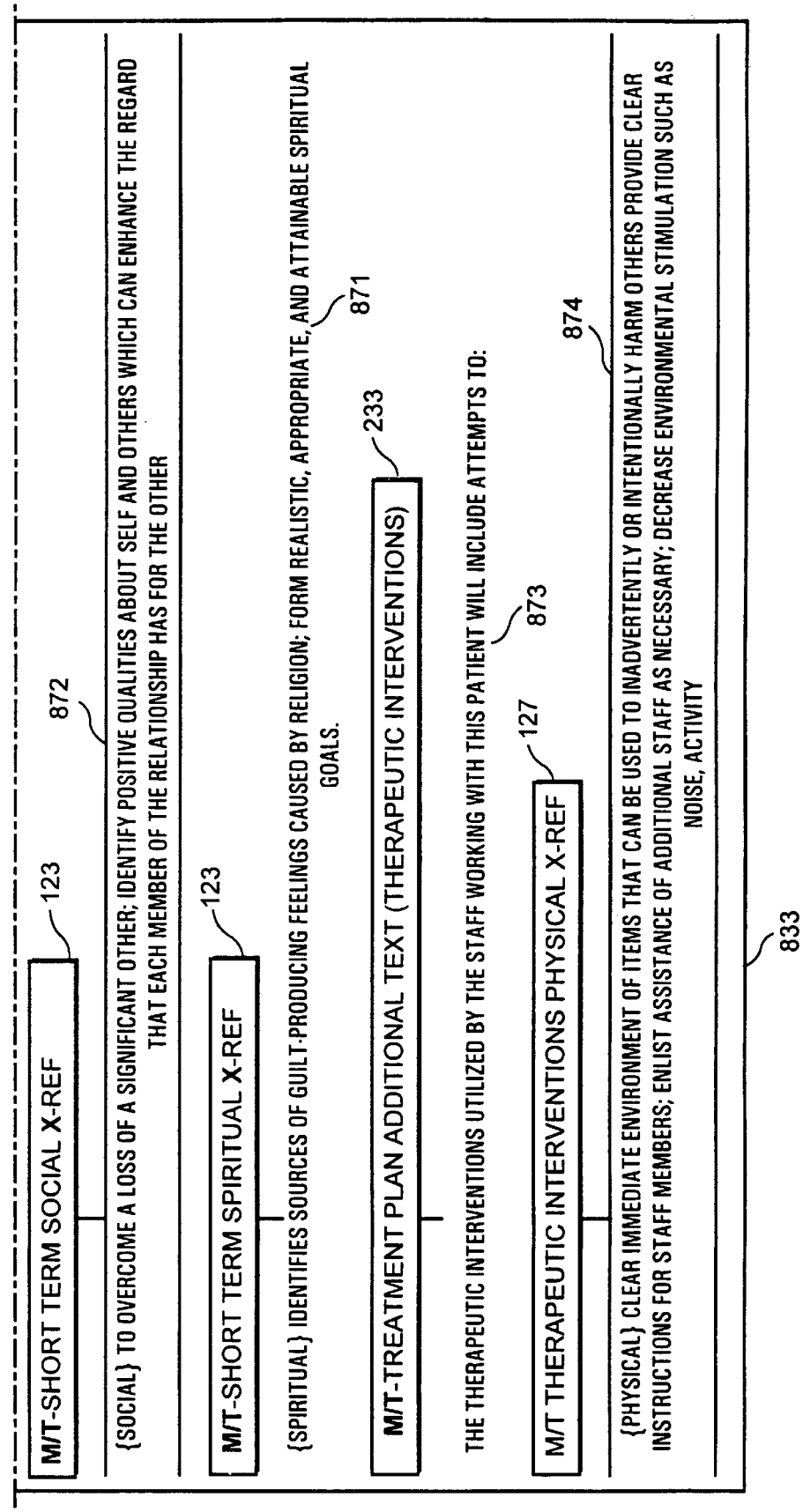
FIG. 14C2

METHOD FOR AUTOMATED COLLECTION OF PSYCHOTHERAPY PATIENT INFORMATION AND GENERATING REPORTS AND TREATMENT PLANS

BACKGROUND OF THE INVENTION

This invention relates to the practice of psychotherapy in an environment whereby insurance companies and HMOs govern, by their payment rules, how patients are cared for. More particularly, this invention deals with a method for automating the gathering of patient information as well as automating documentation, Treatment Plans, and reports required by insurance companies.

In the United States, especially in the last eight years with the explosive growth of managed care and increasingly where Medicare or Medicaid pays for treatment, the administration of psychotherapy is driven by insurance companies. These companies seek to minimize the cost of treatment and demand rigorous documentation by the care provider. As a result, care providers are forced to spend less time with patients and to spend more time generating documentation. As might be expected, patient care has deteriorated with caregivers increasing spending more time, money and energy interacting with managed care companies seeking approval and providing justification for initial concurrent and ongoing treatment.

Despite time constraints, the caregiver is expected to interact with a patient, and to make and record observations about patients and their behavior. At some later point, the caregiver must define patient Treatment Plans and generate detailed patient progress reports, typically two pages in length. Treatment Plans and status reports are derived from observations made while the caregiver sees patients. It is not uncommon for a caregiver to see thirty to fifty patients per day.

Under these trying circumstances, the pressure on caregivers is enormous. The caregivers are attempting to provide a high level of individualized care to a multitude of patients in a very short period of time, yet are expected to provide extensive documentation of the progress of each patient. Given the circumstances, patients tend to blur together making it difficult for the caregiver to remember enough detail about each patient to adequately report progress and to devise effective Treatment Plans.

All three parties, the patient, the caregiver, and the insurance company are badly served by the above situation. The patient receives less individualized care than he or she requires. The caregiver is under pressure to produce results and documentation in an inadequate period of time. The insurance agency receives minimal, often generic documentation. What is needed is a method for easing the caregiver's documentation burden so that he or she might be able to spend more quality, focused, unencumbered time with patients. The insurance company demands for rigorous documentation will not change, thus caregivers must be provided with a method that will enable them to produce the extensive documentation required in less time.

OBJECTS AND SUMMARY OF THE INVENTION

It is therefore an object of the invention to provide psychotherapy caregivers with an apparatus that will enable them to produce the detailed documentation demanded of them by insurance companies quickly and with little effort.

It is a further object of the invention that the above apparatus should be highly portable allowing caregivers to carry the invention to patients.

It is a further object of the invention to provide caregivers with an apparatus to generate individualized multiple alternative Treatment Plans for each patient so that the caregiver might better define an optimal Treatment Plan.

It is further an object of the invention to construct the above apparatus so that it is adaptable to individuals and groups so that patients may be tracked through multiple therapeutic environments.

It is further an object of the invention to share, in appropriate settings where confidentiality can be protected, information with colleagues so that patient treatment may be improved and to facilitate teaching of less experienced staff.

It is further an object of the invention to construct the above apparatus so complete patient histories, including billing, are complied in a database as the caregiver uses the invention It is further an object of the invention to format reports in such a way that patient privacy is protected while report recipients, i.e. insurance companies, receive adequate patient condition documentation.

These and further objects are attained by a computerized method and apparatus which automatedly generates various reports for a psychotherapy provider. These reports include Treatment Plans, progress reports, scheduling reports and billing reports. The progress reports include a Progress Note which incorporates various selected data into a report for the insurance company. As much of the data is selected from menus, the resulting report can maintain much patient privacy while being satisfactory to the insurance company. More private information can be stored separately in Expanded Text. A Treatment Plan is generated using the various selected data with respect to subsets of emotional factors, intellectual factors, physical factors, social factors, and spiritual factor& These subsets may be chosen randomly or with some periodic selection.

FIG. 1 shows a block diagram of the basic therapeutic process. A first step is problem identification. As might be expected, problem identification is vitally important because a misstep at this point will waste time and can even lead to an improper Treatment Plan that might not benefit the patient or could even harm the patient. Problem identification is difficult because a patient may have little or no idea of the real nature of his or her problem(s). It is up to the caregiver to accurately diagnose the true nature of the patient's problem(s) through interaction and observation of the patient and by gathering information from collateral sources.

A next step is to make an assessment of the identified problem In assessing the problem, the caregiver will want to define the problem more concisely, try to find a precipitating event, and find out what the problem means to the patient. Throughout the problem identification and assessment steps, the caregiver will record observations about the patient, typically by taking notes on a computer, by tape recorder, dictation or by hand.

As shown in FIG. 1, a next step is to make a formal record of observations. This usually is performed after seeing a patient, and may include a reexamination of the problem identification and assessment steps. At this point, a caregiver must make a decision to continue or to end treatment. If continued treatment is indicated, the caregiver will define short-term objectives and long-term treatment goals then construct Treatment Plans to accomplish these goals.

A final step is Treatment Plan implementation. FIG. 1 shows the therapeutic process as a closed loop system with problem identification as the next step after treatment implementation. While this is a simplification, as is the whole of FIG. 1, overall it is an accurate representation of the process.

After Treatment Plan implementation, the caregiver must decide if the Treatment Plan is beneficial and should be continued, or if it should be modified or abandoned. As shown by FIG. 1, the effectiveness of the Treatment Plan is determined through repeating the process of FIG. 1.

The present invention uses portable devices such as laptop computers to streamline the caregiver's record keeping throughout the process of FIG. 1. Additionally, the invention's Treatment Plan generation facility acts as a panel of experts aiding the caregiver with expert advice.

BRIEF DESCRIPTION OF THE DRAWINGS

FIG. 1 is a flowchart delineating the basic actions of the psychotherapeutic process.

FIG. 4 is a block diagram detailing elements of the invention's historical database.

FIG. 6 is a flowchart showing options from the invention's main menu.

FIG. 10 is a flowchart showing the process for scheduling individual patients.

FIG. 13 is a diagram of the invention as implemented in a network environment.

FIGS. 14A, 14B, 14C, and 14D show the fields of a Treatment Plan Note with sources of information for populating fields indicated

DETAILED DESCRIPTION OF THE PREFERRED EMBODIMENT

Before beginning the description of the drawings, it should be noted that the invention, as presently configured, is used with a device such as a computer or a palm corder. The computer includes all conventional components such as memory, storage, a CPU, a display, a keyboard and a mouse. As described hereinafter, the various selections are preferably made by pull-down menus or similar devices as is common with WINDOWS® based programs. As envisioned, the caregiver will make rounds then use such devices to generate reports, then dump the reports into a central database. Wherever possible, the invention uses pull-down menus, option boxes, and radio buttons to reduce keyboarding and data entry time.

As stated earlier, FIG. 1 shows the psychotherapy process as a feedback loop. Because FIG. 1 is a simplification of the process, it does not show the caregiver's constant assessment of the information received directly from the patient or from notes. Nonetheless, the feedback loop model shown is an accurate reflection of the basic processes of psychotherapy whatever the theoretical school. An examination of the role of the present invention in the process of FIG. 1 aids in an understanding of both the invention and its utility.

Figure 7:
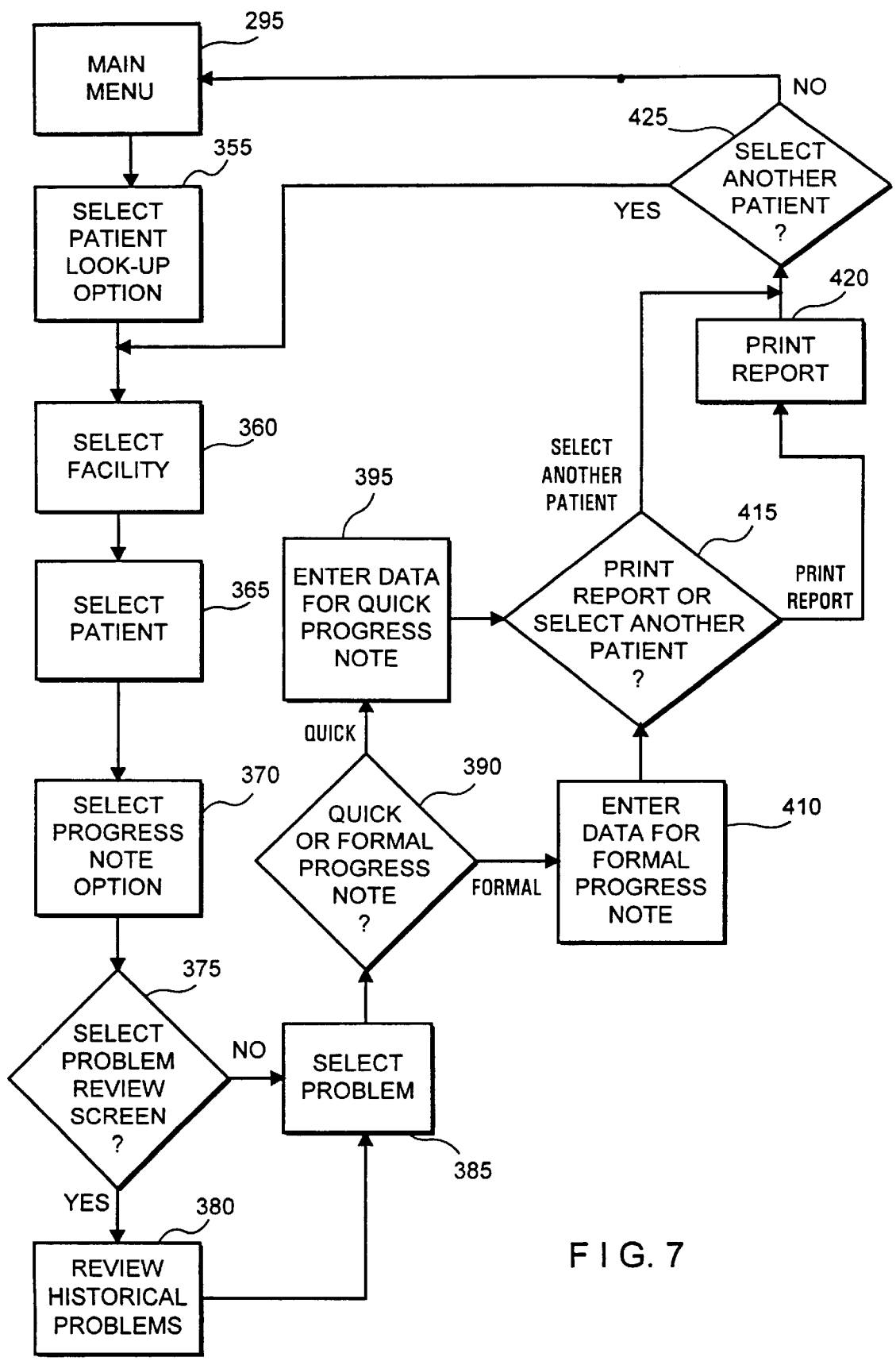
FIG. 7 is a flowchart showing the process for generating Progress Notes.

As per the method of the invention, a caregiver will typically have begun a Progress Note, the result of the process of FIG. 7, after a session with the patient. The caregiver selects the patient and enters the rest of the required bookkeeping data via pull-down menus. The caregiver will then move onto the problem identification process 10 as shown in FIG. 1.

Figure 3:
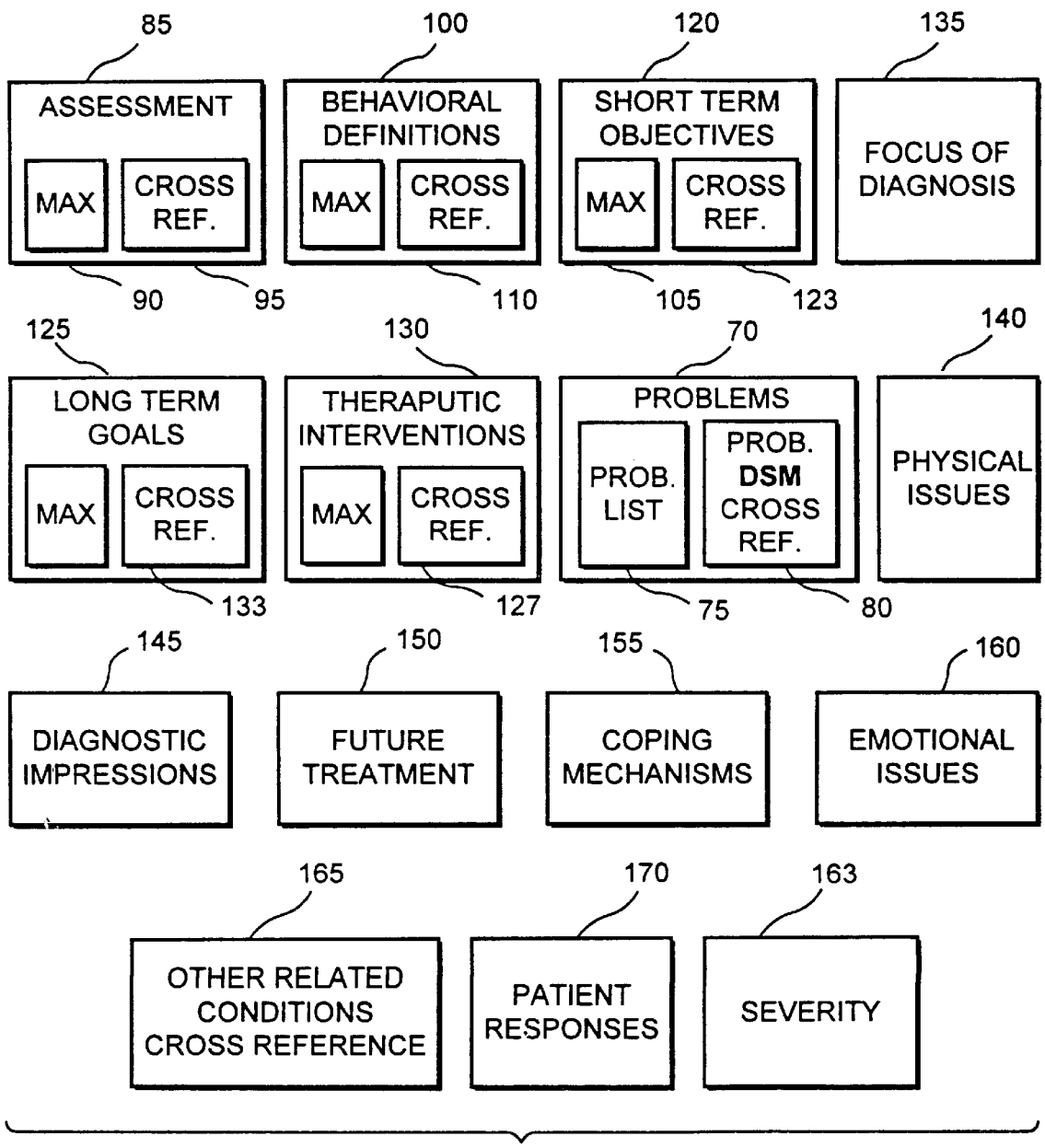
FIG. 3 is a block diagram detailing elements of the encyclopedia of the invention.

Problems are selected from a pull-down menu of 60 possible problems, item 75 as shown in FIG. 3, and Item 1 of the appendix (the appendix delineating a typical problem list). The relatively small size of the database required to describe a patient's problems facilitates a compact, fast-running program Additionally, by providing a concise list of problems, the method and apparatus gives the caregiver a global view of possible problems without overwhelming him or her.

Before a caregiver selects a problem, the method and apparatus can provide a history of patient problems from the Patient Problems Cross-Reference element item 210 as shown in FIG. 4. This feature is helpful in the problem identification and assessment stages 10 and 15 as shown in FIG. 1. Conceptually, the role of the method and apparatus is that of an advisor as opposed to a solution or answer provider. The patient history is meant to stimulate the caregiver's own thinking about the patient's problem, not to force caregiver thinking in any single direction.

As described previously, assessment 15 as shown in FIG. 1 involves direct interaction with, and observation of, the patient. However, the caregiver constantly assesses the validity of his or her observations, the validity of treatment goals, and the validity of Treatment Plans, thus assessment is not limited to item 15.

Patients are not static. Their problems are often in a state of flux, thus treatment objectives and Treatment Plans may be appropriate one day and less relevant the next day. For this reason, the method and apparatus is designed to stimulate caregiver thought processes so that the caregiver may better respond to the changing needs of the patient.

The next step shown in FIG. 1 is recording observations 20. The caregiver will typically use the Quick Note format because of time constraints. Having entered the problem, the caregiver will then indicate the problem severity by selecting from a scale of one to five on a pull down menu with one being least severe and five being most severe. Next the caregiver will select from an Other Related Conditions pull down menu. This information comes from item 165 as shown in FIG. 3 and is keyed to the cited problem, and describes situations that are typically related to the problem Because of the linkage to the problem, those conditions that are relevant to the problem will appear first in the pull down menu.

The caregiver will then select a focus of diagnosis from a pull down menu. This information comes from item 135 as shown in FIG. 3 and is not keyed to the problem The focus of diagnosis simply defines the type of interaction with the patient. Typically, these might be an intake interview, a reassessment after hospitalization, or psychoanalytically informed treatments.

The caregiver will then select a behavioral definition from a pull-down menu. The behavioral definition is a global description of the patient's condition and comes from the treatment encyclopedia data block 100 as shown in FIG. 3. Behavioral definitions are keyed to problems; thus the pull-down menu first displays those behavioral definitions that are relevant to the problem The behavioral definitions in the treatment encyclopedia are culled from medical literature and will be readily accepted and understood by those reviewing the Progress Note.

Next, the caregiver will select an emotional issue which the caregiver deems is a relevant stimulus or precipitant to the problem(s) being addressed in that session from the treatment encyclopedia data block 160 as shown in FIG. 3. The emotional issue is also selected from a pull-down menu, but it is not keyed to the problem. Like the behavioral definitions, the emotional issue section of the treatment encyclopedia was collected from medical literature. The caregiver will then select a physical issue, if relevant from a pull-down menu. Physical issues, i.e., medical problems or conditions, are not keyed to any particular problem and come from the physical issues part of the treatment encyclopedia 140 as shown in FIG. 3. Physical issues are classified by ICD-9 codes.

Next, the caregiver selects a coping mechanism, which is the patient's defensive or adaptive style. Again, this item is selected from a pull-down menu. Coping mechanisms come from the treatment encyclopedia 155 as shown in FIG. 3, and are not keyed to the problem Finally, the caregiver will select patient responses from 170 as shown in FIG. 3 and select an immediate future treatment(s) from 150 as shown in FIG. 3. Both the patient response and future treatment are selected from pull-down menus and are not keyed to a particular problem.

Taken alone, the problem, the problem severity, behavioral definition, emotional issue, physical issue, focus of diagnosis, other related conditions, coping mechanism patient response, and suggested future treatment might seem generic, something like medical boilerplate. However, when viewed as a group in totality, these selected items give a complete picture of the patient's condition and progress while protecting the patient's right to privacy. Through this means, the caregiver can give an insurance company or government agency good documentation without betraying any confidences that are so crucial to the caregiver-patient relationship.

To finish the Progress Note, the caregiver has the option of entering a brief note via the keyboard or by a speech recognition chip in a palm corder type device. This note, called Expanded Text in the method of the invention, allows the caregiver to makes specific comments about sensitive but important data about the patient. This data is stored separately in the historical record section, item 250 as shown in FIG. 4. Access to this information is restricted to the patient's caregiver or to other caregivers. Outside agencies do not have access to this material, and to further protect the patient's privacy, this material can be redacted.

The caregiver may, particularly after an initial session, enter formal diagnostic psychological and medical information using the Formal Progress Note 410 as shown in FIG. 7. This is done via a pull down list of DSM-IV and ICD-9 codes. Specific medical problems, procedures, or hospitalizations may be recorded by selecting the relevant code and entering starting and ending dates. Similarly, medications may be tracked and updated as necessary using these codes.

The generic information described earlier provides excellent documentation for outside agencies while protecting them from the liability of inappropriate release of confidential patient information. Caregivers, on the other hand, need the highly personal information from the Expanded Text to aid them in their search for clues to patient behavior.

The time required to complete the short form Progress Note is brief. The caregiver need only select nine items from pull down menus and type or dictate a brief comment to fully document the session with the patient and present a thorough report on the patient's condition. These items, (1) problem, (2) severity, (3) focus of diagnosis, (4) other related conditions, (5) behavioral definitions, (6) emotional issues, (7) physical issues, (8) patient response, and (9) future treatment are all accessed via pull-down menus. Given experience with the method and apparatus, a caregiver should be able to complete the process in three to five minutes. The resulting short form Progress Note becomes part of the patient's history and is stored in that data block 195 as shown in FIG. 4, except for the Expanded Text which is stored in the Progress Notes Expanded Text block 250 as shown in FIG. 4.

After completing the Progress Note, the caregiver would likely move on to formulating a Treatment Plan, which nay be done manually or automatically. A Treatment Plan includes advice of a future or prospective nature for the caregiver. However first a decision must be made to continue or end treatment, items 35 and 30 as shown in FIG. 1 respectively. Most of the time, continuation is the obvious action to take, but with the pressure on funds for treatment, caregivers may be forced to spend their time with those who would benefit most from treatment. The caregiver may consult the Progress Note patient history 195 as shown in FIG. 4 as an aid in making this decision.

Figure 8:
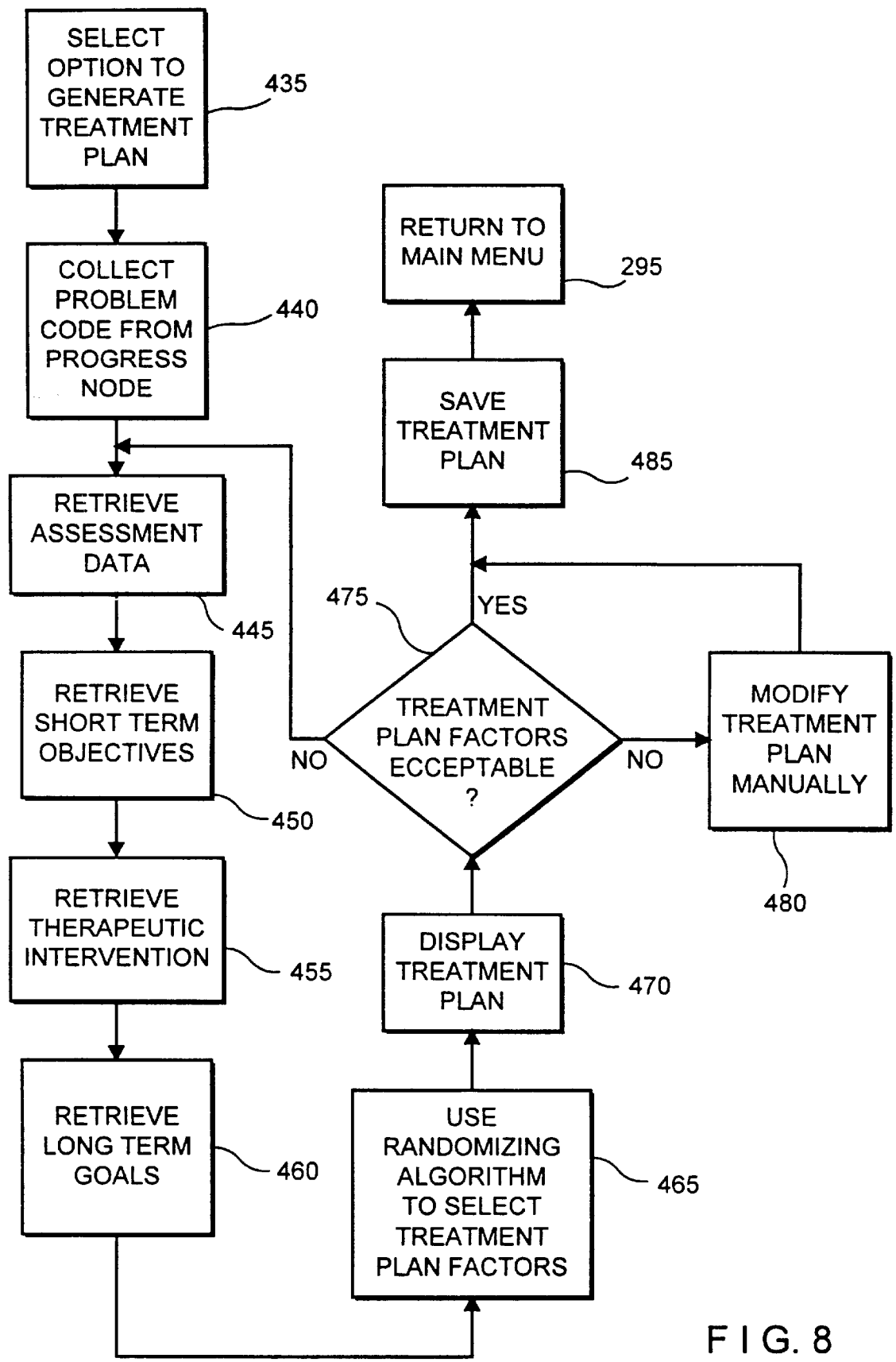
FIG. 8 is a flowchart showing the process for generating a Treatment Plan.

If a decision is made to continue treatment, the caregiver needs to define objectives and goals. At this point, the caregiver might review behavioral definitions, short term objective, therapeutic intervention and assessment reference files from the treatment encyclopedia. Alternatively, the caregiver may opt to instruct the method and apparatus to automatically generate the Treatment Plan (process described below) which is then combined with the "live" data previously entered by the caretaker, resulting in the "Treatment Plan Note." With the aid of this information and the Treatment Plan options generated by the method and apparatus as shown in FIG. 8, the caregiver will define a Treatment Plan 40 as shown in FIG. 1 that best fits the present needs of the patient.

In item 45 as shown in FIG. 1, the caregiver implements the therapeutic intervention defined in the Treatment Plan of item 40. As shown by FIG. 1, the therapeutic process begins again after the therapeutic intervention. The patient's reaction or lack of reaction to the intervention is assessed and acted upon by the caregiver through the process of FIG. 1, thus completing the feedback loop.

Throughout the process of FIG. 1, the method and apparatus have aided the caregiver by greatly speeding up the documentation process. Instead of the burdensome, oftentimes redundant, and time consuming process of filling out forms by hand or from a keyboard, the caregiver need only select options from pull-down menus. Additionally, the caregiver need no longer rack his or her mind for descriptive terms and language and treatment ideas. The pull-down menus and Treatment Plans generated by the method and apparatus provide caregivers with stimulation, structure, and alternatives.

Figure 2:
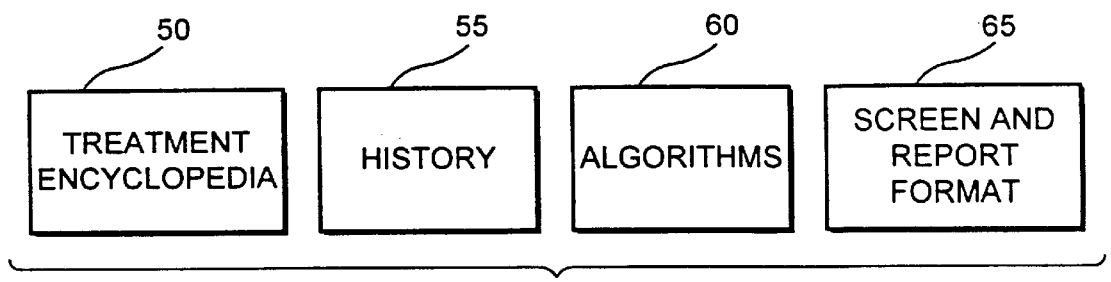
FIG. 2 is a block diagram depicting the basic elements of the invention.

FIG. 2 shows the basic data blocks that are used by the method and apparatus of the present invention. The treatment encyclopedia 50 contains information used for reference and for formulating Treatment Plans. The information in the treatment encyclopedia comes from accepted medical literature and professional experience. The contents of the treatment encyclopedia are described more fully in the discussion of FIG. 3.

Item 55 contains historical data. The various data subgroups are described in detail with the discussion of FIG. 4, but generally, item 55 is the record of the method and apparatus of the invention. The historic database is added to constantly by the method of the invention. Any new data such as Progress Notes, new patients, new caregivers, updated personal or insurance information, collateral information or contacts or billing records become part of the data of item 55. Through accessing the data of item 55, a caregiver can pull up a complete history of a patient or groups of patients with complete records of Progress Notes and Treatment Plans and billing records.

Item 60 contains the algorithms used to formulate Treatment Plans as well as those algorithms specific to the method and apparatus of the invention that enable interaction between the various screens and generation of reports. Item 65 contains the data required to format screens and reports. The various sub-groups of item 65 are described in detail with the discussion of FIG. 5.

The data blocks of FIG. 2 are divided by function and as such are not dependent on any particular operating system However, all the data blocks described are needed for the method and apparatus of the invention to provide the functional aspects of data gathering, report generation, and Treatment Plan generation described in this specification.

FIG. 3 shows the details of the treatment encyclopedia. This data block is the primary reference for the method and apparatus of the invention. Item 70, the problem block, contains two sub groups, 75 the list of 60 problems shown as Item One in the appendix, and a Diagnostic and Statistical Manual cross reference 80. Problem list 75 describes the problems displayed by patients in the majority of cases. The problems are denoted with specific code numbers. As an example amnesia has a code of 100, anger has a code of 200, and anxiety has a code of 500. Item 80, the DSM cross reference, defines the problems of item 75 in standard DSM-IV codes so outside agencies such as insurance companies will find the problems listed in item 75 acceptable.

Assessment data block 85, long term goal data block 125, short term objectives block 120 and therapeutic interventions block 130 are divided into sub groups consisting of emotional factors, intellectual factors, physical factors, social factors, and spiritual factors. These five factors along with problem list 75 serve to clarify and simplify the description of the bewildering number of conditions displayed by patients. The aforementioned five factors encompass all areas that can effect patients and must be allowed for when dealing with the patient. By defining assessment data, short term objectives, long term goals, and therapeutic interventions in terms of these factors, the method and apparatus of the invention gives caregivers a vocabulary to define a patient's condition and treatment options concisely using easy-to-use pull-down menus thus greatly simplifying the caregiver's work.

These data blocks are keyed to the problem data block 75. Thus, when a caregiver accesses these data blocks, those factors keyed to the problem being examined appear first in the pull-down menus. This prioritizing off actors serves to focus the caregiver and prevents him or her from being overwhelmed by data.

Assessment step 15 as shown in FIG. 1 is essentially a refinement and focusing of problem diagnosis step 10 as shown in FIG. 1. Through the assessment process, the caregiver attempts to define the exact nature of the problem and its intensity. Data block 95 as shown in FIG. 3 provides the caregiver with a vocabulary for assessment in the five dimensions, emotional, intellectual, physical, social and spiritual Data block 95 has been modified and refined so that it reflects an accurate assessment of a patient in the great majority of cases. Going with the philosophy of the invention as an advisor and aid to the caregiver, the invention suggests possibilities, but the caregiver has the final word in defining the nature of the patient's problems.

Assessment criteria are also important in the scheme of the invention because they factor in the Treatment Plan generation operation. When the caregiver generates a Treatment Plan FIG. 8, the basic process is as follows. The invention creates Treatment Plans through the presentation of behavioral definitions from block 110 as shown in FIG. 3, assessment data from block 95 as shown in FIG. 3, short-term objectives from block 123 as shown in FIG. 3, therapeutic interventions from block 127 as shown in FIG. 3, and long term goals from block 133 as shown in FIG. 3. These elements are keyed to the problem code. Thus, if the problem code is anger item 200 in the problem list in the appendix, those elements of data blocks that refer to anger are selected as possibilities. The cross reference blocks for assessment 95, short term objectives 123, long term goals 133, and therapeutic interventions 127 refer to five dimensions of a patient's condition. The five dimensions are physical emotional intellectual, social and spiritual As an example, short term objectives 120 as shown in FIG. 3 has two elements, the cross reference section 123 and the Max section 105. The cross reference section links the short term objectives data block to problems data block 70 in five different dimensions, physical intellectual, emotional social and spiritual Thus when a Treatment Plan is created, the short term objectives section will have problem focused information for all five dimensions.

The Max section 105 defines limits for the randomizing algorithm used in creation of Treatment Plans. Datablocks 85, 100, 125, and 130 also have Max elements in them. The Max elements are statistical stings of the incidence of particular aspects in those datablocks. These values were defined originally when setting up the program. Maxs have been altered over the life of the program as a database of patient histories has developed. As per the method of the invention, Maxs serve to inform the algorithm used in formulating Treatment Plans as to the extent of the possible information selections linked to any one problem Thus the problem of anger may have thirty informational selections associated with it, while different problems will have more or less information selections. The Max informs the Treatment Plan algorithm about the extent of the information pool.

Datablocks physical issues 140, emotional issues 160, severity 163, coping mechanisms 155, patient responses 170, and other related conditions 165, focus of diagnosis 135, and future treatments 150, all of FIG. 3, provide additional information to the caregiver and are available to the caregiver at anytime. There is, of course, some overlap. For example, many physical issues, emotional issues, coping mechanisms and patient responses are common to those having problems with anger and those having problems with anxiety.

To generate the Treatment Plan, the device, via the relational database program, takes text and "boiler-plate"

relating to various fields from a master table of "Treatment Plan-Additional Text" 233 FIG. 4 and merges the input entered by the user (including input data chosen from the menus), as selected by the randomizing or similar routine, therewith.

The information presented to the caregiver both serves to stimulate the caregiver into thinking long appropriate lines and prevents the caregiver from being overwhelmed by possibilities. This last aspect is critical because the problems presented by patients are complex, with severe time constraints and intense interactions with colleagues in treatment teams serving to complicate matters even further. Taken together, these factors can leave a caregiver feeling blocked and overwhelmed. By presenting a constrained listing of information to the caregiver, the invention helps the caregiver to focus and clarifies issues concerning diagnosis and selection of Treatment Plans.

In other words, the current or historical data is entered by the caregiver and combined with prospective advisory data (as retrieved from the treatment encyclopedia as indexed by the randomizing or similar function) to generate a Treatment Plan Note is the most comprehensive and useful end result.

Moreover, particularly with regard to the Treatment Plan, the device may be implemented as using artificial intelligence using the tables and mechanisms described above. In particular, the "severity" function can be used to delimit the data available to the randomizing (or similar selection) algorithms in the generation of the Treatment Plans. Further, an internal feedback looping process can be used to enhance the functionality and usefulness of this method and apparatus in clinical settings. With the addition on an "outcome" button (with associated underlying mechanisms and elements, such as the master table of outcomes for the Treatment Plan Note, queries, forms, reports, etc.) on the Quick Entry Screen for individual Progress Notes and the Adjust "Group" Attendance/ Participation screens, the caregiver can provide feedback to the method and apparatus in the form of, firstly, results (in quantifiable and analyzable form) of the therapeutic inventions utilized and, secondly, the specific inventions utilized in the prior individual or group session.

By a system of tracking, quantifying and analyzing these results and methods (that is, therapeutic interventions and future treatments), the method and apparatus of the invention, with artificial intelligence implemented, can, in effect, monitor itself and by accurately recording the entered data and computer generated Treatment Plan Note, "learn" via artificial intelligence, which particular strategies (that is, therapeutic interventions, future treatments) can best address particular "problems of the day" short term objectives and long term goals.

FIG. 4 shows the elements of the invention's historical database. These data blocks are keyed to individual patients so that the history of each patient can be defined in the context of these elements. This database evolves with use. Most of the elements require little in the way of explanation.

The patient master table 240 contains information about the patient such as the name, sex,birth date, social security number as well as the patient's Medicare and Medicaid numbers. The key element is the social security number because every patient must have a unique social security number. Billing history 175 is simply the complete historical record of each patient's billing history. Caregiver's can access the complete record, the billing history for any given time period, or the most recent billing. Billing histories may be accessed via the main menu screen, patient look up screens, or from Progress Note screens.

The physician record element 180 is the historical record of patient medical doctors other than the caregiver. Typically a patient would have a medical doctor addressing physical problems while the mental health caregiver supervises patient mental and emotional problems. With an aging population, many of a patient's physical problems will have a profound impact on the patient's mental state and vice versa. Thus, the caregiver and physician need work closely. Because patients may have multiple physicians or may change physicians, the caregiver must have access, whenever feasible, to the complete historic physician record to obtain all patient data including but not limited to hospital, rehab and medication information.

The caregiver record 200 is similar to the physician record in that a patient may have dealings with different caregivers. It may be important for the present caregiver to speak with the caregiver of a previous time so that the caregiver can define a patient's history in terms outside his or her own experience. Patients, particularly in nursing homes, retirement communities, or residential care facilities may have required treatment over the course of several years. It is important for a new caregiver to understand the experience of previous caregivers thus the need for the historical record of caregivers. Additionally, the caregiver record has links to billing histories thus allowing analysis of caregiver productivity.

Facility record 220 and service location record 235 are simply the historic records of locations where patients are treated and the location of the caregiver's office respectively. The facility record comes into play when the caregiver uses the patient look up screen. The caregiver first selects the facility from then selects the patient from the record of those patients at the facility. The patient master table 240 contains those records that define the patient such as sex, birth date, Medicare and Medicaid number and social security number. When the caregiver chooses the patient, those information fields are filled in automatically from this table. Facility and patient selection use drop down menus and are rapid and effective way of identifying the patient. The service location record comes into play when defining caregiver billing records.

The patient physical issues cross reference 190 is the historical record of patient physical problems. Because physical issues can directly influence a patient's mental state, caregiver's must have access to a complete history of the physical issues confronting the patient. Patient problems cross reference 210 contains the history of patient problems recorded from Progress Notes.

The Progress Notes section 195 is the historical record of Progress Notes written throughout the course of the patient's treatment. This database contains Progress Notes made by all caregivers not just the current caregiver. This accumulated collection of notes provides an important record of the course of a patient's condition and reaction to therapy. The caregiver's ready access to this material throughout the process of the invention enables more informed problem selection and assessment as well as an examination of the progress of the patient's mental state through the course of treatment.

As described earlier, the Progress Notes Expanded Text section 250 as shown in FIG. 4 is that part of a Progress Note where a caregiver has entered a personal observation and DSMIV diagnosis focused on the problem of the day. This section is linked to the Progress Notes section, but is kept as a separate database so that a caregiver need not fear accidentally making this information available to an outside agency.

Progress Notes Additional Text 245 and Treatment Plan Additional Text 233 contain phrases that are used in conjunction with elements from the treatment encyclopedia and data from Progress Notes to fill out fields in reports. This will be explained in detail with the discussion of FIGS. 14A, 14B, 14C, and 14D.

The various group histories, group master 185, group participants 205, group session master 225, and group session participant Progress Notes 215 are used for scheduling and for tracking a patient's progress through the group therapy environment. The caregiver needs to be able to examine these historical records in detail to understand the patient's behavior more thoroughly because patient's often react differently in a group environment than they do one-on-one with the caregiver.

To better understand the patient's reaction to these differing environments, the caregiver must know the participants in each group. It is possible that a patient reacts badly to a certain individual or a certain type of behavior displayed by other individuals. A patient might be outgoing and vocal in a sheltered setting, but may be withdrawn or aggressive in the more stressful group environment. Unless the caregiver has access to detailed histories of a patient's group participation, he or she will be unable to understand and treat the full range of the patient's problems in the context of their known strengths and abilities.

Figure 5:
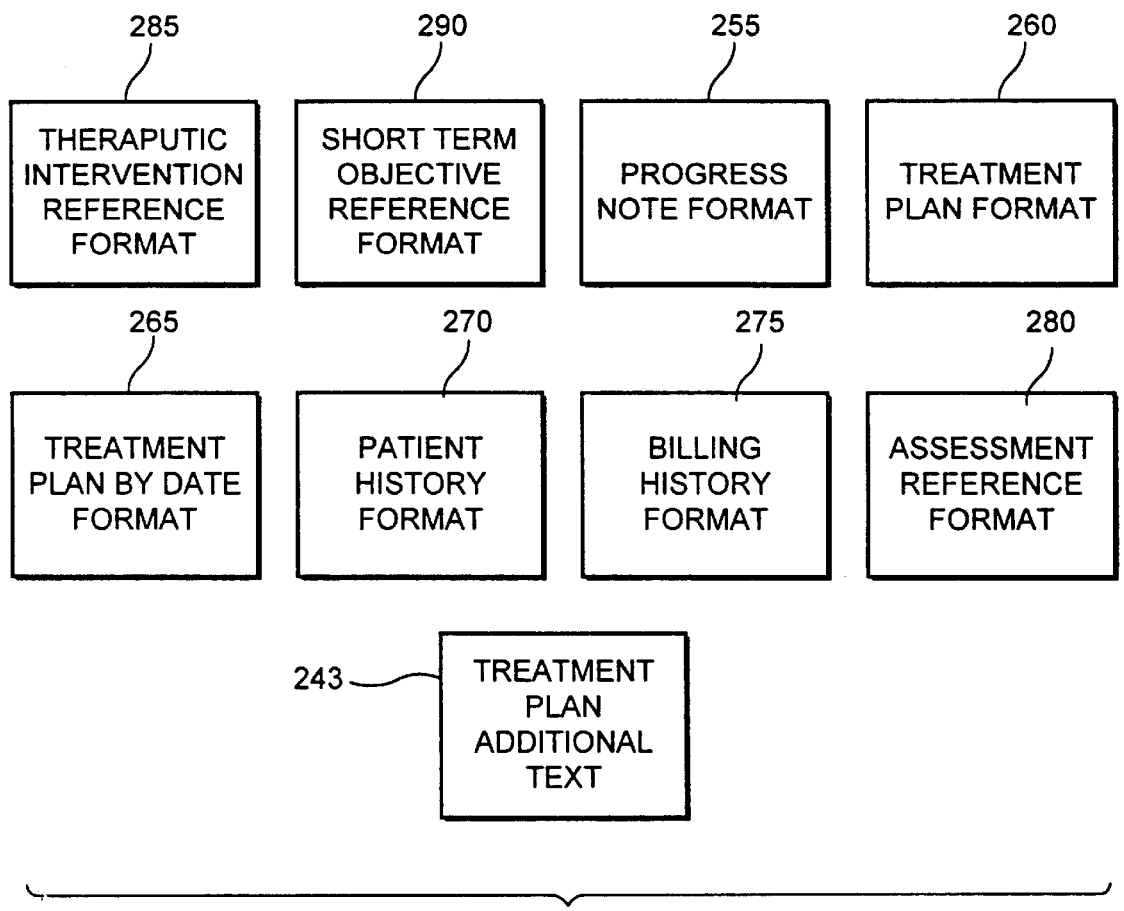
FIG. 5 is a block diagram showing format groups used with the present invention.

FIG. 5 shows the collection of formats used by the invention to define screen layout and interaction with other elements of the invention. All formats are designed so that the caregiver can move from screen to screen as quickly as possible and to minimize caregiver data entry chores. Drop-down menus are used wherever possible, i.e. for patient selection or for reference and review of histories. Additionally, formats such as Progress Notes are designed with as much "boilerplate" as possible so that caregivers need only fill in the blanks to give a complete and accurate description of a patient's condition.

The Progress Note formats 255 FIG. 5 and Progress Notes Additional Text 245 FIG. 4 are designed to work in concert to minimize caregiver data entry. The Progress Note format section 255 defines the overall structure of the Progress Note with the Progress Note Additional Text section 245 serving to provide the boilerplate language for the Quick Note and the four page Formal Progress Note input screens and reports. As in descriptions of other data block sections of the invention, the actual formatting structures are dependent on the chosen operating system, thus this specification will include a generic description of those data blocks needed to implement the invention.

Assessment reference format 280, short term objective reference format 290, and therapeutic intervention reference format 285 are designed to present those elements in five dimensions: emotional intellectual, physical, social and spiritual, cross referenced to the problem being worked on. As presently configured, the invention presents this information in a pull-down menu format so that the caregiver may browse through the possible selections easily and make selections by a single action such as a mouse click.

The Treatment Plan format 260 defines the Treatment Plan screen layout and also defines the linkages of the Treatment Plan screen to other parts of the invention. The Treatment Plan by Date format 265 defines screen layout and links so that the caregiver can call up the historic record of Treatment Plans and access any time period desired. Patient history format 270 and billing history format 275 are similar to the Treatment Plan by Date format in that these formats are designed to let the caregiver access a patient's history and billing history for any time period quickly and easily.

FIG. 6 is a block diagram of the options available to caregivers from the main menu screen of the invention. From the main menu screen 295, the caregiver has four options, enter data 300, generate reports 302, transfer files 305, and examine reference files 310. The Enter Data option 300 is the take off point for most of the caregiver's work. From this option, the caregiver deals with individual patients 315, works with groups 320, schedules patient therapy sessions 325, and updates physician or caregiver information 330.

The Generate Reports option 302 allows the caregiver to generate reports such as a semi-annual review of a patient's problems 316, lists of patients seen by a caregiver over a specific time period 322, and a review of patient intakes over a given time period 326.

The Transfer Files option 305 allows caregivers to transfer files from one device to another. Typically, a caregiver would use this option when downloading work done on a laptop or a palm corder to a network at the end of a shift. Another typical use is accessing and downloading records from a network server to a caregiver's laptop. The transfer files option is not only a convenience, but is necessary for historical database compilation purposes. As mentioned previously, caregivers need complete access to patient histories. The file transfer option enables automatic construction of the patient histories through downloading of progress reports and other current records.

The Examine Reference Files option 310 allows caregivers to move directly to Assessment Reference Files 335, Short Term Objective Reference Files 340, and Therapeutic Intervention Reference Files 345. Typically, a caregiver might access these files to gain insight about a particular behavior or problem displayed by a patient. As mentioned previously, these datablocks are referenced to particular problems and are defined in five aspects, emotional, intellectual, physical, social, and spiritual Thus, for nearly any type of problem, a caregiver can quickly pull up and examine a compilation of assessment criteria, short term goals, and therapeutic interventions keyed specifically to that problem. The value of this rapid access to complete information cannot be overstated given the time constraints faced by caregivers. In those situations where the caregiver is blocked and needs stimulation or where the caregiver needs to verify an assumption, this aspect of the invention is invaluable.

FIG. 7 shows the process of the Progress Note. As mentioned previously, there are two Progress Note forms, the Quick Note and the Formal Progress Note. The Quick Note is the standard caregiver working note. This form of Progress Note contains sufficient data to be an excellent source of information for the caregiver and other caregivers who might treat the patient. The Formal Progress Note provides more detailed documentation and is meant for use by outside agencies such as insurance companies, or for detailed record keeping in medical hospital or clinical settings. Additionally, the formal note might be used for research or educational purposes. The format of the Formal Progress Note combines readily accepted medical boilerplate with "fill-in-the-blank" information from pull-down menus to define a patient's status and progress in a manner that will be complete and useful to outside agencies and for internal record keeping.

FIG. 7 describes the process for both types of notes, the difference in the two being primary length, type of boilerplate, and resulting pull-down menus used for the two. The caregiver begins from the main menu screen 295 and moves from there to the select patient look-up option 355. The caregiver selects the facility from a pull-down menu 360, then selects the patient from a pull-down menu showing the patients at the facility 365.

In item 370, the caregiver selects the Progress Notes option, then selects a problem of the day. In most cases, the caregiver will have already determined the problem when interacting with the patient. Nonetheless, the caregiver may want to review a history of the patient's problems to get a historic perspective on the patient's progress. Item 375 indicates the option to review the patient's historical problems 380 or to move straight to problem selection 385.

At this point, the caregiver must decide whether to proceed to the Quick Note 395 or the Formal Progress Note 390. After the caregiver chooses the desired format, the process is basically the same for both formats. With the quick form, the caregiver enters data 395 using pull-down menus for various "fill-in-the-blank" questions and might enter a more personal observation in the expanded notes section. Typically, the caregiver would first indicate problem severity, select other related conditions, and focus of diagnosis, and then select a behavioral definition(s). As previously described, Behavioral Definitions, item 100 as shown in FIG. 3, are global descriptions of a behavior and are keyed to selected problems. Thus, those behavioral definitions keyed to the problem selected at item 385 will appear first in the pull-down menu Next, the caregiver would select a relevant emotional issue from a pull-down menu originating from data block 160 as shown in FIG. 3. Emotional issues are not linked to any particular problem because a problem may or may not be a direct manifestation of an emotional issue. However, emotional issues and precipitating events that lead to emotional issues, are important clues to a patient's behavior thus should be included in a Progress Note.

Next, the caregiver might select a physical issue from a pull-down menu. The physical issue data originates from the Physical Issues datablock 140 as shown in FIG. 3. So that the physical issue data is universally acceptable, physical issues are expressed in terms of standard ICD-9 definitions and codes. For convenience, colloquial descriptions are used as well, i.e. arthritic, diabetic, and/or cardiac conditions. As with emotional issues, physical issues are not linked to any particular problem. A patient problem may or may not be a direct manifestation of a physical issue. However, as with emotional issues, physical issues are vital to an understanding of a patient's behavior.

The caregiver might then select a coping mechanism, (adaptive style), displayed by the patient from a pull down menu. This information originates in data block 155 as shown in FIG. 3, and is not keyed to the problem selected at item 385. As with the emotional and physical issues selection, a patient's coping mechanism can be an important clue to a patient's progress, yet may or may not be a direct manifestation of the problem selected at 385.

At this point the care giver might select a patient response to treatment and a possible future treatment. Both items are selected from pull-down menus and originate from items 170 and 150 as shown in FIG. 3 respectively. Again, neither item is linked to the problem of 385 yet both items are important records for the therapy process.

The items just described, problem severity, focus of diagnosis, other related conditions, behavioral definitions, emotional issues, physical issues, coping mechanisms, patient responses, and suggested future treatments are all options available in the Quick Note. Taken together these items form an effective snapshot of the patient at the time of the evaluation. If these items are combined with a caregiver personal observation in the Expanded Note section of the Quick Note, the resulting record is a detailed description of the patient that becomes an invaluable reference for the caregiver and any other caregivers entrusted with the care of that particular patient. With very little practice, the caregiver will be able to create this precise record in a matter of three to five minutes.

After completing the Progress Note 395, the next step is to decide whether or not to print the report 415. If printing is desired, the caregiver selects the Print Report option 420. If not, the caregiver moves directly to the decision to select another patient 425.

If the caregiver decides to continue with another patient, the process loops back to the Select Facility option 360. If the caregiver chooses to end the Progress Note process, he or she returns to the main menu 295 for other options such as patient scheduling 325 as shown in FIG. 6.

If at decision point 390, the caregiver had chosen to select a Formal Progress Note, the process is exactly the same except that the format of the formal note is more detailed and contains a lengthy section on assessment data, short term objectives, long term goals, and therapeutic interventions. Because the assessment data, short term objectives, and therapeutic interventions are keyed to the problem, those assessment criteria related to the problem appear first in the pull-down menus.

As described earlier, the assessment data originate from data block 85 as shown in FIG. 3, and are expressed in five dimensions, emotional, intellectual, physical, social and spiritual. The Formal Progress Note allows the caregiver to make selections in all five areas. The Formal Progress Note also permits selections in all five areas for short term objectives and therapeutic interventions. As with the assessment data section, short term objectives and therapeutic interventions are keyed to the selected problem. If the selected problem were anger, the caregiver would have the opportunity to select comments about assessment data, short-term objectives, and therapeutic interventions in all five areas for anger (physical, emotional, intellectual, social, and spiritual).

After completion of the Formal Progress Note, the caregiver moves through the process as described earlier. Decisions are made concerning printing the report 415 or selecting another patient 425. Thus, other than differences in report length, the Formal Progress Note process mirrors the Quick Note process.

The Treatment Plan process of FIG. 8 is a vital component of the therapeutic loop of FIG. 1. With the creation of the Progress Note, the caregiver has defined the patient's current state. With the Treatment Plan, the caregiver defines the nature of hoped for patient improvement and a suggested method for achieving progress.

In going with the philosophy of the invention as an advisor rather than a solution provider, the process of FIG. 8 provides suggested Treatment Plans for the caregiver to review. The caregiver is not expected to take Treatment Plan suggestions as instructions to be followed exactly. Instead, the caregiver uses the suggested Treatment Plans as a stimulus to define an optimal treatment program In the process of FIG. 8, the caregiver may look at several alternative Treatment Plan suggestions before deciding on a course of action.

The process of the invention for generating Treatment Plans involves selecting assessment data, short term goals, therapeutic interventions and long term goals keyed to problems defined in Progress Note reports. If, as would be typical the caregiver generates the Treatment Plan in concert with a Progress Note, the problem so defined would be the focus of the Treatment Plan, and the result of the process defined as a Treatment Plan Note. If the caregiver decides to skip the Treatment Plan step, the invention automatically generates a Treatment Plan for any Progress Note that does not have an attendant Treatment Plan when the caregiver next accesses the Treatment Plan option.

Additionally, the invention will generate a Treatment Plan for each of the problems associated with the patient defined in a Progress Note. Thus, if the caregiver identified anger and depression as problems for a given session, the invention would generate one Treatment Plan for anger and one for depression for that given therapy session.

Treatment Plan generation begins when the caregiver selects the Treatment Plan option from the main menu screen 435 as shown in FIG. 8. The next step in FIG. 8 is to select the problem that is to be the focus of the Treatment Plan 440. If the caregiver is operating out of the main menu after completing a group of Progress Notes, the invention automatically defaults to the problem already selected in the Progress Note for that given session. With items 445, 450, 455, and 460, the invention retrieves assessment data, short term objectives, therapeutic interventions, and long term goals that are keyed to the selected problem. This collection of data is gathered from data blocks 85, 120, 130, and 125 respectively, all from the therapeutic encyclopedia of FIG. 3.

As previously described, assessment data, short term objectives, therapeutic interventions, and long term goals are defined in emotional, intellectual, physical, social, and spiritual terms. As presently configured, a randomizing algorithm 465 as shown in FIG. 8 selects two items from each of the five factors from items 445, 450, and 455 then selects two factors from 460. The invention then displays that result as Treatment Plan options 470. Alternatively, the randomizing algorithm could be replaced with systematic, periodic or manual selection of a subset of emotional, intellectual, physical, social and spiritual terms.

After reviewing the treatment options offered in item 470, the caregiver must decide if the options are acceptable 475. At this point the caregiver has three choices. The options may be deemed acceptable, the caregiver may selectively edit out irrelevant or inappropriate material or the caregiver may opt to define an entirely new Treatment Plan by cycling through the randomization algorithm again. If the caregiver decides to edit the plan, he or she win optimize the Treatment Plan then save it 485 and return to the main menu screen 295. If the caregiver has decided to opt for a new Treatment Plan, the process loops around to item 445.

Experience has shown the process of FIG. 8 to be an effective method for generating Treatment Plan Notes. All options presented in 470 are keyed to the problem thus are relevant. Additionally, patient problems are complex and there is never one correct Treatment Plan. Many treatment approaches are valid and caregivers have found the many options suggested by the process of FIG. 8 to be helpful in defining an optimum Treatment Plan for patients. Additionally, patients are not static. Their problems can change dramatically from day to day, and the limitless number of Treatment Plan options offered by the invention can aid caregivers in their attempts to stay abreast of changing patient conditions and anticipated events or reactions to treatment.

As a refinement of the invention, a severity factor has been incorporated into the invention as a problem modifier . When a caregiver selects a problem for a Progress Note, he or she indicates the severity of the problem on a scale of one to five. This has the effect of weighting the linkages between a problem and the items selected for Treatment Plan generation. As a result of this process, the range of items selected during the process of 445, 450, 455, and 460 is narrowed and are more closely aligned to the patient profile. This is not to say that the philosophy of the invention has changed. The options presented in item 470 should be only regarded as suggested options. It is up to the caregiver to decide on the course of treatment. However, the narrowed spectrum of possibilities allows the invention to present a more tightly focused group of options to the caregiver.

Figure 9:
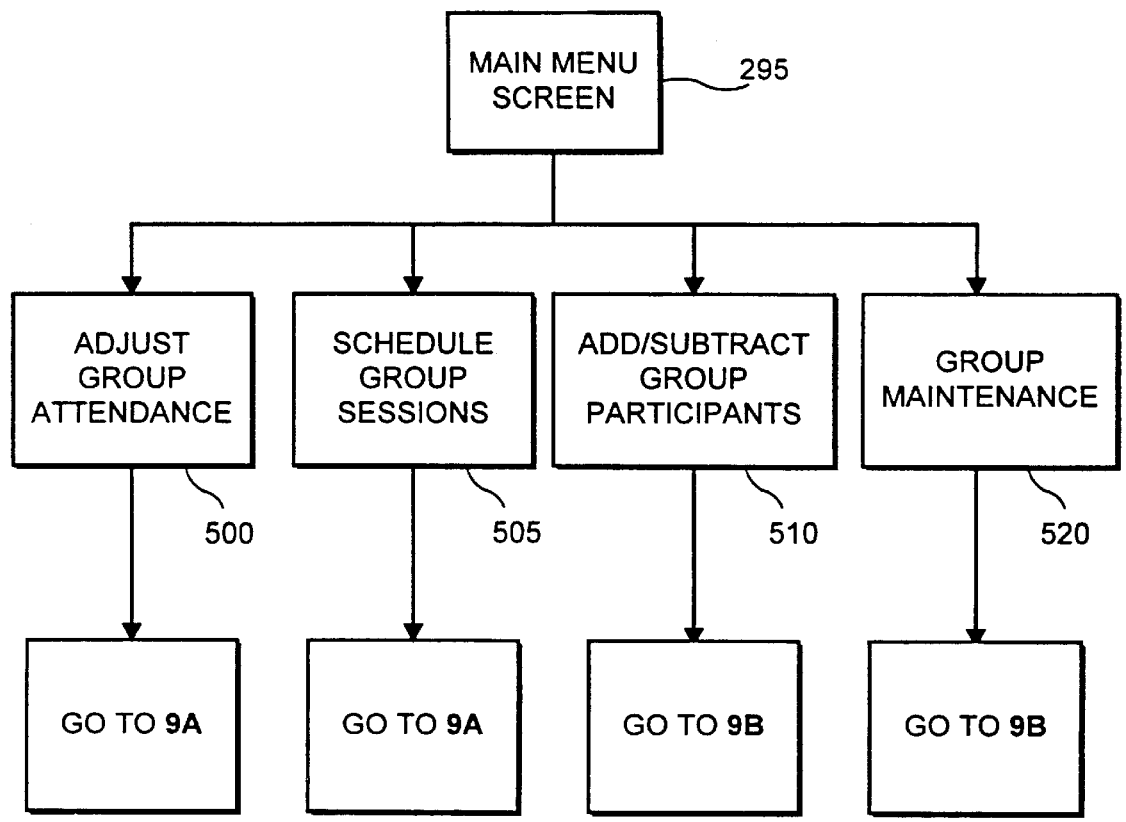
FIG. 9 is a flowchart showing the various processes for scheduling and maintaining groups.

FIG. 9 details the courses open to caregivers when choosing from the groups option 320 as shown in FIG. 3. From the main menu screen 295 as shown in FIG. 9, caregivers can select from the group maintenance option 520, the add group participants option 510, the schedule group sessions/group Progress Notes option 505, or the adjust group attendance option 500. Taken together, these four options provide all the tools needed for caregivers to create, maintain and schedule therapy groups.

The group maintenance option 520 is used to set up and decommission groups. With option 520, the structure of the group is set up. The group is populated with patients using option 510, add group participants. The caregiver begins the process of option 520 by selecting the chosen facility from a pull down menu 525 as shown in FIG. 9B. The caregiver names the group entering the name in the data entry screen 530 FIG. 9B, then decides if another group is to be entered 535 FIG. 9B. If so, the process loops around to the select facility option 525. If the caregiver wishes to exit the process of 520, he or she selects to return to the main menu 540 FIG. 9B.

At this point, the caregiver would populate the group just created using the add group participants option 510 FIG. 9B. The caregiver begins this process by selecting a facility and the group name from pull-down menus 545 as shown in FIG. 9B, then selects the name of the group participant by selecting a facility and patient name from pull-down menus 550 as shown in FIG. 9B. The reason the facility must be selected a second time is that patients from one location may take part in groups at another location.

The caregiver then moves on to the add or delete option 555 as shown in FIG. 9B. Since the process of 510 is used both to add and delete patients from groups, the caregiver must indicate his or her intention on the screen of item 555. At this point, the caregiver indicates if another patient is to be added or deleted from a group. If the caregiver wants to continue the process of 510, there are two options. The caregiver can continue to work with the present group by moving to the select patient option 550. If work with a different group is desired, the caregiver moves to the select facility and group option 545. If the caregiver wishes to exit the process of 510, he or she returns to the main menu 565 as shown in FIG. 9B.

Figure 9A:
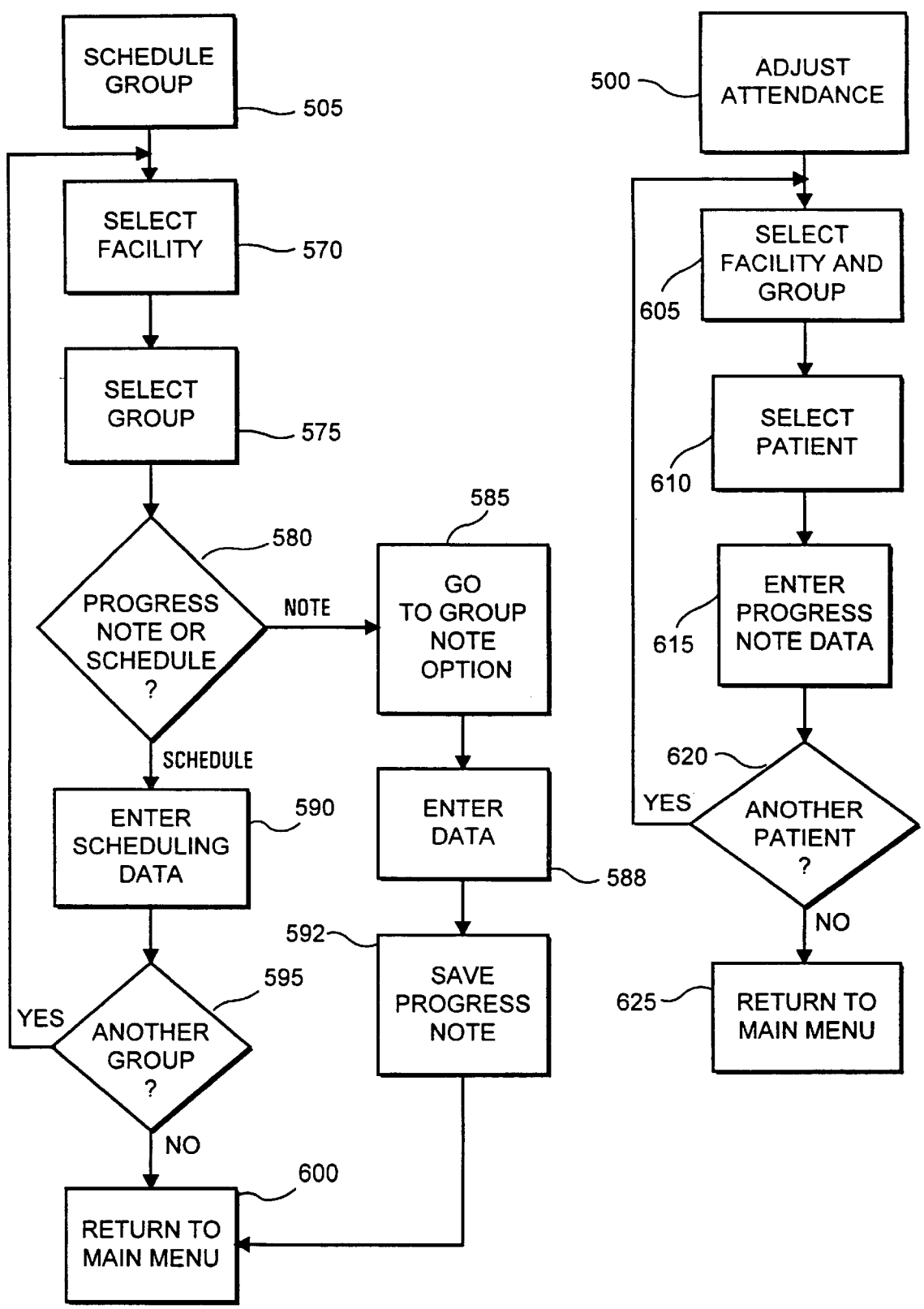
FIG. 9A shows a flowchart for adjusting group attendance and a flowchart for scheduling group sessions.
Figure 9B:
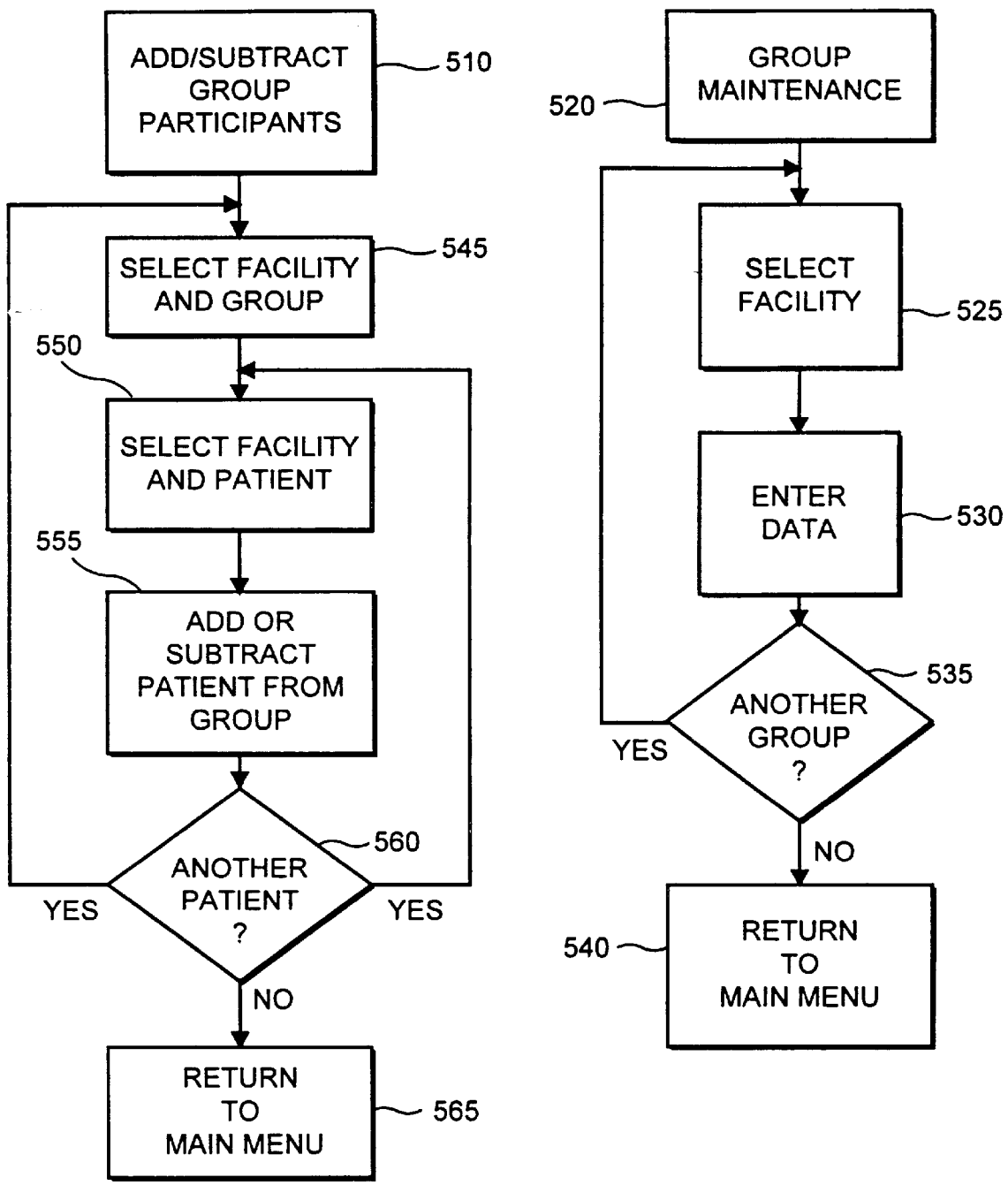
FIG. 9B shows a flowchart for adding or subtracting group participants and a flowchart for group maintenance.

After populating a group with patients, the caregiver moves on to the process scheduling the group by selecting option 505 as shown in FIG. 9A. Option 505 serves a double duty as it is used to set group schedules and as an entry to the Group Progress Note option. The process of 505 as shown in FIG. 9A begins with the caregiver selecting the facility 570 as shown in FIG. 9A and the group 575 through the use of pull down menus. At this point 580 as shown in FIG. 9A, the caregiver indicates whether the objective is to start a Group Progress Note by selecting the Group Progress Note option 585 or to move to the scheduling option 590.

If the caregiver chooses the scheduling option, he or she enters a starting time and date and the invention automatically schedules a preset number of group meetings at that time slot. With item 595, the caregiver indicates whether another group is to be scheduled, in which case the invention loops back to item 570. If the other option is selected at 595, the caregiver goes back to the main menu 600.

The process of the Group Progress Note 585 is slightly different from an individual Progress Note. The dynamics of a group's interaction are complex compared to reactions of individuals within the group. Thus, data entry 588 consists of the caregiver moving directly to an expanded note section where the behavior of the group, (including process notes and therapeutic group issues), as well as significant individual patient reactions are noted.

When the note is saved 592, it automatically is placed in the record of all patients who are scheduled to participate in a group. Typically, a caregiver then returns to the main menu 600 to record individual Progress Notes for all members of the group through selection of adjust group attendance option 500 as shown in FIG. 9. Thus, a patient record will contain the Group Progress Note delineating the dynamics of the group and the group's reaction to the group discussion in an individual Progress Note detailing the patient's reaction to the dynamics of the group and his or her progress in dealing with specific problems within the context of the group therapeutic experience. This information is contained in a second Expanded Text section. Thus the Progress Note for a patient attending a group will have the general Expanded Text note common to all who attended the group and an individualized Progress Note focusing on the patient. The invention is structured so that the group expanded note is saved then automatically added to each individual Progress Note as the caregiver writes the note.

The adjust group attendance option 500 as shown in FIG. 9A is accessed from the main menu. After selecting option 500, the caregiver will select the facility and the group from pull-down menus 605. Next, the caregiver selects the patient from a pull down menu displaying patients in the group 610, and enters the data for the Progress Note. The Progress Note follows the quick Progress Note process of FIG. 7 including identification and selection of assessment data, patient's participation level, participation quality, "at risk" status, overall theme of the group and the type of interventions specifically directed towards the patient with most of the input coming from pull down menus. The problem selected for the individual Progress Note reflects the problem presented by the patient to the group on that given day and time of treatment and/or the patient's reaction to the group and its dynamics.

For example the group discussion may be about a sense of loss, but an individual patient's reaction to the group might well be anger. Thus, the caregiver would select anger for the individual Progress Note. The information from the pull-down menus will describe the patient's reaction to the group in general terms, and the expanded note section will document details and possible explanations for the patient's behavior from the caregiver's point of view.

This note taken together with the Group Progress Note provides a detailed picture of the patient's reaction to the complex dynamics of the group. Because the time required to produce the Group Progress Note is divided by the number of participants, the composite time required to create a Group Progress Note and an individual Progress Note should be only slightly more than three to five minutes.

FIG. 10 shows the process for scheduling appointments for individual patients. The process begins from the main menu screen 295 with the selection of the individual scheduler option 630. Next the caregiver selects the facility and the patient from pull-down menus 635, then enters the desired schedule data 690. As with the group scheduling data entry screen 590 as shown in FIG. 9, the invention permits automated scheduling of appointments after entering an initial date.

With item 645, the caregiver decides to schedule another patient or to return to the main menu 650. If the caregiver decides to schedule another patient, the process loops around to item 635 so that the caregiver can select another facility and patient.

Figure 11:
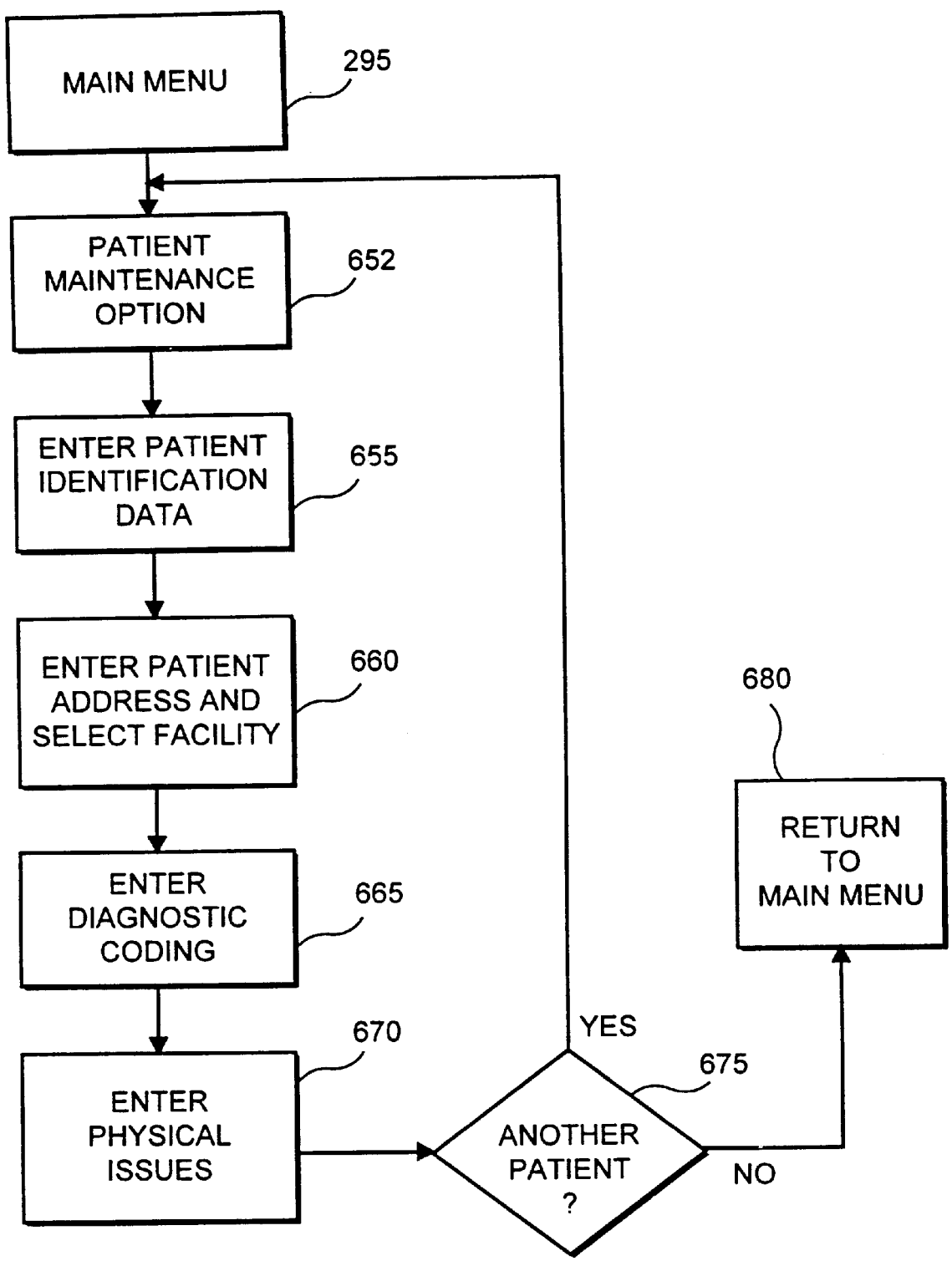
FIG. 11 is a flowchart showing the process for maintaining individual patients.

FIG. 11 shows the process for patient enrollment. The process begins with the main menu screen 295. The caregiver then selects the patient maintenance option 652, and moves on to entering patient identification data 655. Patient identification data typically will consist of entering the patient's name, social security number, date of birth, gender and may include the patient's Medicare and Medicaid number. Additionally, identification data will include date of entry into facility or treatment, marital status, past hospitalizations, relevant medical history, and involved family members or friends.

Next, the caregiver enters the patient's address and the location of facility where the patient will be housed 660. Although pull-down menus are used whenever possible throughout the actions represented by 655 and 660, most of the data will have to be entered by keyboard. The caregiver then moves on to entering the initial assessment data 665. This section makes full use of pull-down menus to describe the patient's condition and select the proper diagnostic code. A final step is to enter data on relevant physical issues 670. Here again, pull down menus are used to speed data entry. From this point, the caregiver moves on to item 675 where a decision is made to return to the main menu 680 or to enroll another patient. If the latter option is chosen, the process loops around to patient maintenance option 652.

Figure 12:
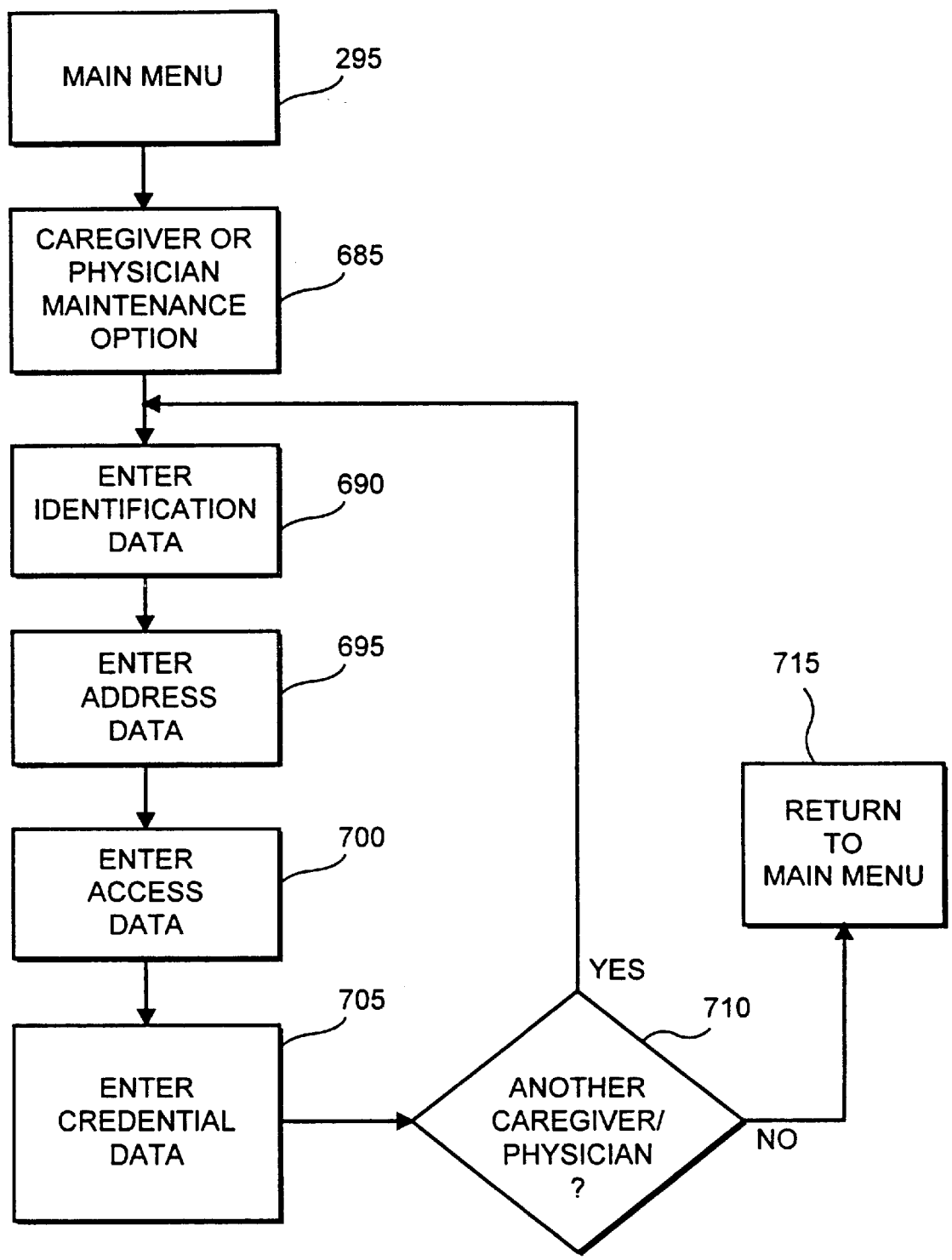
FIG. 12 is a flowchart showing the caregiver and physician maintenance process.

The process of FIG. 12, the caregiver or physician maintenance option is similar to the process of FIG. 11. The process starts from the main menu screen 295 with the next step being selection of the caregiver/physician maintenance option 685. For the enter identification information step 690, most of the information is entered via the keyboard, but pull-down menus are used where possible to speed up the process. The next steps, entering the address 695, access numbers 700, and credentials 705 are made via keyboarding as there is little opportunity to use pull-down menus. With item 710, the caregiver returns to the main menu 715 or enters data for a new caregiver/physician 690.

The processes of FIGS. 11 and 12 are the most keyboard intensive tasks experienced with the invention. However, these are one time efforts and should not take longer than five to ten minutes per person. Thus, these aspects of the invention will not compromise the overall time savings offered by the invention.

The invention may be used in a stand-alone mode or, as shown by FIG. 13, a central server could be used as a database in a local or wide area network application. The main advantage to this approach is the rapid compilation of a large historical database. A database compiled by multiple caregivers becomes an invaluable tool for doing research.

FIG. 13 shows a central server 800 acting as a database, a workstation 830 connected via a local area network 825, as well as a laptop computer 810 connected via a modem. Both the workstation and the laptop would be independent of the server 800 except for downloading data at the end of the day or accessing data on an irregular basis. Device 820 represents a terminal in a network environment wherein the terminal is interacting in real time with the server 800. In this case only the application is on the terminal. All records are accessed via the server. The advantage to this is that different users my be granted different access privileges.

The invention is presently configured as a relational database using a series of tables with common fields to implement the relational functionality. This configuration was selected for ease of implementation, flexibility and for the amenability to statistical and other types of inquiries. The product used as a base for the database is MICROSOFT ACCESS®. This is not to say that the invention is tied to the relational database model any more than it is tied to any particular operating system. That said, the invention works very smoothly and quickly as presently configured.

Figure 14D:
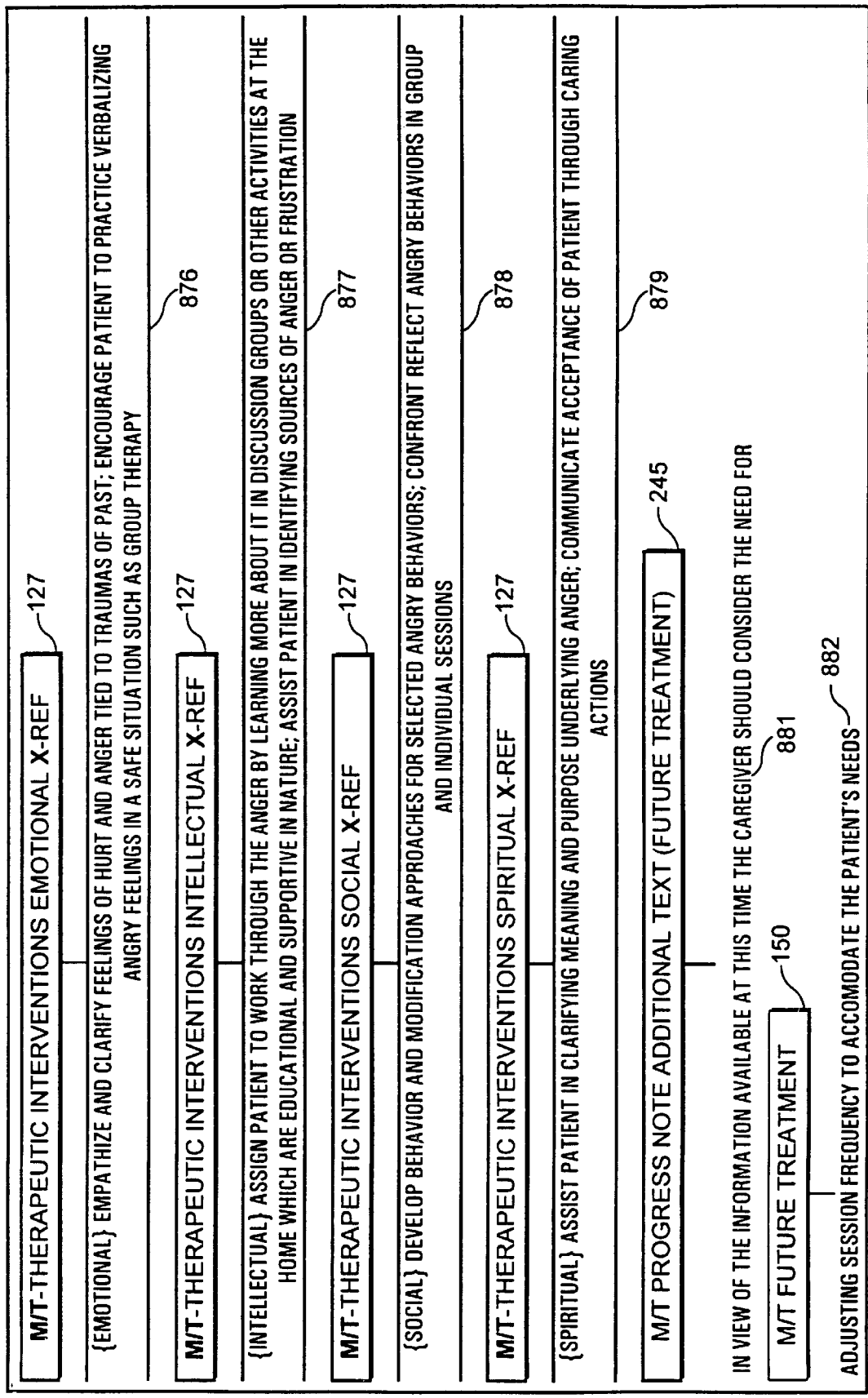

FIGS. 14A, B, C, and D show the fields that make up a Treatment Plan Note report and the sources for the data populating the fields. This report first identifies the patient 827 FIG. 14A, displays a history of past problems 831 FIG. 14A, displays symptoms displayed by the patient during the session being reported on 832 FIGS. 14A and 14B, then ends with the Treatment Plan recommendations 833 FIGS. 14B, 14C, and 14D. FIG. 14A shows the first part of a Treatment Plan Note. The word "patient" 802 comes from the Treatment Plan format element 260 FIG. 5 and is always displayed with a Treatment Plan Note. The accompanying name of the patient AAANestor AAATestor 803 comes from the patient master table 240 FIG. 4 as does much of the basic patient identification data. As shown, the patient's social security number 809, gender 804, Medicare and Medicaid numbers 807, date of birth 811, and facility name 806 all come from the patient master table 240. All these elements are keyed to the social security number which is referenced by the session ID number 812 which comes from the Progress Notes table 195 FIG. 4.

Thus when a Treatment Plan Note is generated, for a particular session, the social security number of the patient linked to that secession ID number implements the relationship between the two tables and facilitates the population of the previously discussed patient information fields. This also includes the problem DSM-IV Codes 814 and 816 that come from the patient master table as well as the attendant verbal descriptions 817 and 818, that come from the problem master table 75 FIG. 3.

The caregiver code 821 and the name of the caregiver 823 come from the Progress Note table 195 and the caregiver table 200 respectively both of FIG. 4. Thus when this treatment report is generated, the caregiver code related to the session ID number from the Progress Note table 195 provides the link to the caregiver name from table 200 FIG. 4, thus completing the patient identification section 827 FIG. 14A. The patient history section 831 receives data from two sources, the patient problem cross-reference table 210 FIG. 4 and the problem table 75 FIG. 3. Item 210 contains the problem codes, 100.001 item 837 being an example, for any problems reported in a Progress Notes. These problems are linked to the patient's social security number, thus are accessed and displayed when the Treatment Plan Note is generated. Item 839 is an example of a verbal description of a problem linked to the problem codes. These descriptions come from the problem table 75 FIG. 3.

The information of section 832 FIGS. 14A and 14B comes from the Progress Notes table 195 FIG. 4. This material is linked to this report with the session ID code 812. When a problem code is saved for the problem of the day in the Progress Note table 195, it results in the population of fields 841 and 843. As an aside, if no data were save in the problem of the day section of the Progress Note table 195, fields 841 and 843 would not be populated and the area in the report would remain blank. As shown in FIG. 14A, item 841 comes from the Progress Notes Additional Text table 245 FIG. 4 and the attendant problem description 843 comes from problem table 75 FIG. 3.

The caregiver's detailed comments 844 come from the Progress Notes Expanded Text table 250. Again these items are linked to the session ID code 812. Boilerplate 846 comes from the Progress Notes extended text table 245 FIG. 4, while the attendant behavioral definition 847 comes from the table of behavioral definitions 100 FIG. 3. Boilerplate statement 849 concerning related conditions comes from the Progress Notes Additional Text table 245 FIG. 4 and the attendant condition comes from the other related conditions table 165 FIG. 3. As in earlier cases, the code for item 851 is stored in the Progress Notes record 195 FIG. 4 and is linked to the session ID 812.

Moving to FIG. 14B, the emotional issue boilerplate 851 comes from the Progress Note Additional Text table 245, as does the physical issues boilerplate 852. The emotional issue entry 853 comes from the emotional issue table 160 FIG. 3 while the physical condition description 864 comes from the physical issues table 140 FIG. 3. These entries complete item 832, that section of the report dealing the patient's condition as observed by the caregiver at the time of the treatment session.

Item 833 FIGS. 14B, 14C, and 14D contains the Treatment Plan. As described earlier, the Treatment Plan is based on the problems observed and noted by the caregiver on the Progress Note. For this report, the problem of the day is depression 843 FIG. 14A. The first section of the Treatment Plan deals with assessment data. This material is displayed in terms of the five dimensions expressed earlier, physical, emotional intellectual, social and spiritual. The section is headed by boilerplate 856 that comes from the Treatment Plan Additional Text element 233 FIG. 4. The assessment issues displayed 857, 858, 859, 861, and 862, all of FIG. 14B, come from the assessment cross reference table item 95 FIG. 3. Two items are described for each assessment issue. As the invention is configured presently, these issues are chosen at random from the pool of data linked to depression in the assessment cross-reference table 95 FIG. 3.

The rest of the Treatment Plan deals with long term goals, short term objectives, therapeutic interventions, and suggested future treatment. As described earlier, the process for populating the data field for long term goals, short term objectives, and therapeutic interventions is keyed to the problem of the day, in this case depression. As is the case for the assessment section above, a randomizing algorithm selects two items from the data pool linked to depression for each category.

Long term goal boilerplate 863 comes from Treatment Plan Additional Text 233 FIG. 4 with the attendant data 864 FIG. 14C coming from the long-term goal cross-reference table 133 FIG. 3. The next section, short term objectives, proceeded by boilerplate 866 which comes from Treatment Plan Additional Text 233 FIG. 4, is displayed in the five dimensions. This data, physical 867, emotional 868, intellectual 869, social 872, and spiritual 871 comes from the short-term objective cross-reference table 123 FIG. 3. As with the process above a randomizing element pulls two selections from the pool linked to each dimension from table 123.

Therapeutic intervention boilerplate 873 comes from the Treatment Plan Additional Text table 233 FIG. 4. As with the short-term objectives, two data selections are made for each of the five dimensions. Physical data 874 FIG. 14C comes from the therapeutic interventions cross-reference table 127 FIG. 3 as does emotional data 876, intellectual data 877, social data 878, and spiritual data 879, all of FIG. 14D. The final section future treatment, is headed by boiler plate 881 from the Progress Notes Additional Text table 245 FIG. 4 with the attendant data 882 coming from the future treatment table 150 FIG. 3

RAMIFICATIONS OF THE INVENTION

The ramifications of the invention are both obvious and subtle. It should be obvious from reading the specification that the invention saves caregivers a great deal of time and energy. What may not be so obvious is the quality of record keeping and report generation possible based on data analysis enabled by the invention. When caregivers must keep records without the stimulation and aid of the present invention, records often become generic because caregivers do not or cannot take time to record relevant observations resulting in records for one patient tending to be similar to another. The focused pull-down menus offered by the present invention relieve caregivers of generating descriptive text while providing them with stimulating multiple choices.

When a caregiver makes a Progress Note entry using the invention, the effect is that of having a panel of experts presenting various possibilities. The caregiver quickly discards those choices that seem inappropriate and selects that which seem reasonable. This multiple choice approach is swift and much less draining than trying to generate descriptive material from scratch. Caregivers get tired, discouraged and/or demoralized, but the structure of the invention forces a caregiver to generate a sharply focused well articulated record.

One must also take into account the pressure to reduce treatment costs in the mental health field. A course often taken is to use either less experienced individuals and or those with lower levels of training as caregivers. As an example, a nurse, a social worker, or some other non-doctoral level treatment professional might replace a doctor as a caregiver. In this environment, the present invention, with its multiple choice, panel of experts approach is effective for training and can help caregivers to become highly effective.

The automatic combination of a group note linked to an individual note in a relational database structure is extremely significant. Patients are complex and the ability to draw on the entire record of a patient's experience and reaction to a group setting provides caregivers with a tool that facilitates defining the real nature of a patient's problems. Additionally, the ability to access a complete, detailed patient history at any time plus the ability to generate Treatment Plan alternatives automatically can only enhance a caregiver's ability to provide more effective patient treatment. Furthermore, because this invention is based on quantitative data, even though it has a textual presentation, it permits unlimited data analysis. These analyses are customizable, detailed, flexible and personalized reports determined solely by the caregiver's and/or institution's clinical requirements and interests. Analysis can be performed against any recorded data. Examples of these reports and data analysis possible include: patients seen by date range, by location and by caregiver; reports of individual and group sessions conducted by caregiver by location; analysis of procedure codes utilized by caregiver by location; and periodic reports including all problems addressed in treatment for patients, all physical and emotional issues, all medications, and hospitalizations.

When all is considered, the present invention simplifies and speeds up the process of patient record keeping, report generation, data and trend analysis while aiding caregivers in their search for optimum Treatment Plans. The records accumulated in the invention's historical database provide a rich source for measuring caregiver and Treatment Plan effectiveness. The information generated by this invention also allows for education and supervision, clinical research and program planning and advanced cost analysis. In short, not only does the present invention increase the efficiency of caregiver record keeping, but also it aids them in their attempts to practice more effective therapy.

Thus the several aforementioned objects and advantages are most effectively attained. Although a single preferred embodiment of the invention has been disclosed and described in detail herein, it should be understood that this invention is in no sense limited thereby and its scope is to be determined by that of the appended claims.

APPENDIX—EXAMPLE OF PROBLEM LIST

| Code | Problem |
| --- | --- |
| 100 | Amnesia |
| 200 | Anger |
| 300 | Anorexia and Bulimia Nervosa |
| 400 | Antisocial Behavior |
| 500 | Anxiety |
| 600 | Alcohol/Chemical Dependence |
| 700 | Alcohol/Chemical Dependence-Relapse |
| 800 | Childhood Traumas |
| 900 | Chronic Pain |
| 1000 | Cognitive Deficits/Confusion |
| 1100 | Compulsions |
| 1200 | Confusion |
| 1300 | Conversions |
| 1400 | Crisis |
| 1500 | Delusions |
| 1600 | Denial |
| 1700 | Dependency |
| 1800 | Depression |
| 1900 | Dissociation |
| 2000 | Eating Disorders |
| 2100 | Education Deficits |
| 2200 | Family Conflicts |
| 2300 | Female Sexual Dysfunction |
| 2400 | Grief/Loss Unresolved |
| 2500 | Guilt |
| 2600 | Hallucinations |
| 2700 | Hyperactivity in Children |
| 2800 | Hypochondriacal Behavior |
| 2900 | Impulse Control Disorder |
| 3000 | Intimate Relationship Conflicts |
| 3100 | Legal Conflicts |
| 3200 | Loneliness/Isolation |
| 3300 | Low Self-Esteem |
| 3400 | Male Sexual Dysfunction |
| 3500 | Malingering |
| 3600 | Mania or Hypomania |
| 3700 | Manic Behavior |
| 3750 | Manipulation |
| 3800 | Medical Issues |
| 3900 | Negative Self-Concept |
| 4000 | Negativism |
| 4100 | Noncompliance |
| 4200 | Obesity |
| 4300 | Obsessions |
| 4400 | Paranoid Ideation |

-continued

| Code | Problem |
| --- | --- |
| 4500 | Passive-Aggressive Behavior |
| 4550 | Personality Disorders |
| 4600 | Phobias |
| 4700 | Psychoticism |
| 4800 | Rape Trauma Syndrome |
| 4850 | Schizophrenia |
| 4900 | Sexual Abuse |
| 5000 | Sleep Disorders |
| 5100 | Social Discomfort |
| 5200 | Somatization |
| 5300 | Spiritual Confusion |
| 5400 | Suicidal Ideation |
| 5500 | Suspiciousness |
| 5600 | Vocational Stress |
| 5700 | Withdrawn Behavior |

What is claimed is:

1. An apparatus for providing historic documentation and prospective treatment advice for a plurality of psychotherapy patients for a psychotherapy provider comprising:
    means for automated collecting and recording of psychotherapy data for the patients, said psychotherapy data being in a plurality of categories, each of said plurality of categories including historic and prospective information;
    means for choosing a subset of at least two categories from said plurality of categories;
    means for storing a database comprising textual data corresponding to a plurality of possible psychotherapy data said data including prospective treatment advice;
    means for referencing into said database by said psychotherapy data in said subset of at least two categories thereby selecting a portion of said textual data including prospective treatment advice; and
    means for combining said portion of said textual data with psychotherapy data including historic data from said means for automated collecting and recording thereby automatically generating at least one historic report and one prospective report.

2. The apparatus of claim 1 wherein the automated collecting and recording of patient psychotherapy data and the automated generation of the report of claim 1 originates from, and is indexed to, a list of possible psychotherapeutic problems.

3. The apparatus of claim 1 wherein at least one report includes a relatively short form patient report and a relatively long term patient report.

4. The apparatus of claim 1 wherein said at least one report includes prospective treatment advice.

5. The apparatus of claim 1 wherein said at least one report includes historic information relating to the psychotherapy patient.

6. The apparatus of claim 1 wherein said at least one report links the historical record of at least two psychotherapy patients.

7. The apparatus of claim 1 wherein said database includes a psychological and psychiatric treatment encyclopedia.

8. The apparatus of claim 7 further including means for updating said treatment encyclopedia.

9. The apparatus of claim 1 further including means for scheduling therapy sessions for individual patients and simultaneously for a group of patients.

10. The apparatus of claim 1 wherein said at least one report includes a billing report.

11. The apparatus of claim 1 wherein said database is a relational database.

12. The apparatus of claim 2 wherein said list of possible psychotherapeutic problems is derived from medical literature and wherein the apparatus further includes means for revising said list of possible psychotherapeutic problems.

13. The apparatus of claim 3 wherein generation of at least one report is automated through menu selections to the psychotherapy provider.

14. The apparatus of claim 7 wherein said treatment encyclopedia includes:
    (a) a list of possible patient problems
    (b) a list of possible behavioral definitions
    (c) a list of possible assessment criteria
    (d) a list of possible short term objectives
    (e) a list of possible long term goals
    (f) a list of possible therapeutic interventions
    (g) a list of possible physical issues
    (h) a list of possible emotional issues
    (i) a list of possible patient coping mechanisms
    (j) a list of possible suggested future treatments
    (j) a list of possible related conditions
    (k) a list of possible patient responses.

15. The apparatus of claim 4 wherein said prospective treatment advice includes at least one set of assessment data, at least one short term objective, at least one therapeutic intervention and at least one long term goal for said at least one report.

16. The apparatus of claim 1 wherein said historic information is available to psychotherapy providers at any time during operation of the apparatus.

17. The apparatus of claim 1 wherein said plurality of categories includes at least emotional factors, physical factors, intellectual factors, social factors, and spiritual factors.

18. The apparatus of claim 2 wherein entries from said list of possible psychotherapy problems can be assigned a severity from a range of severities for each psychotherapy patient.

19. The apparatus of claim 18 wherein said assigned severities serve as a weighting factor for the selection of prospective treatment advice.

20. The apparatus of claim 1 wherein said means for choosing a subset of categories includes pseudo-random selection.

21. The apparatus of claim 1 wherein said means for choosing a subset of categories includes periodic selection.

22. The apparatus of claim 1 wherein the means for automated collecting and recording of psychotherapy data is linked to said database comprising textual data through network means.

23. An apparatus for providing historic documentation and prospective treatment advice for a plurality of psychotherapy patients for a psychotherapy provider comprising:
    means for automated collecting and recording of psychotherapy data for the patients, said psychotherapy data being in a plurality of categories, each of said plurality of categories including historic and prospective information;
    means for choosing at least two subsets of categories from said plurality of categories;
    means for storing a database comprising textual data corresponding to a plurality of possible psychotherapy data said data including prospective treatment advice;

means for referencing into said database by said psychotherapy data in said at least two subsets of categories thereby selecting a portion of said textual data including prospective treatment advice; and means for combining said portion of said textual data with psychotherapy data including historic data from said means for automated collecting and recording thereby automatically generating at least one historic report and one prospective report.

24. An apparatus for providing historic documentation and prospective treatment advice for a plurality of psychotherapy patients for a psychotherapy provider comprising:

means for automated collecting and recording of psychotherapy data for the patients, said psychotherapy data being in a plurality of categories, each of said plurality of categories including historic and prospective information;

processing means for pseudo-randomly choosing a subset of categories from said plurality of categories;

means for storing a database comprising textual data corresponding to a plurality of possible psychotherapy data said data including prospective treatment advice;

means for referencing into said database by said psychotherapy data in said subset of categories thereby selecting a portion of said textual data including prospective treatment advice; and means for combining said portion of said textual data with psychotherapy data including historic data from said means for automated collecting and recording thereby automatically generating at least one historic report and one prospective report.

25. An apparatus for providing historic documentation and prospective treatment advice for a plurality of psychotherapy patients for a psychotherapy provider comprising:

means for automated collecting and recording of psychotherapy data for the patients, said psychotherapy data being in a plurality of categories, each of said plurality of categories including historic and prospective information, said categories including emotional, physical, intellectual, social and spiritual categories;

means for choosing a subset of categories from said plurality of categories;

means for storing a database comprising textual data corresponding to a plurality of possible psychotherapy data said data including prospective treatment advice;

means for referencing into said database by said psychotherapy data in said subset of categories thereby selecting a portion of said textual data including prospective treatment advice; and means for combining said portion of said textual data with psychotherapy data including historic data from said means for automated collecting and recording thereby automatically generating at least one historic report and one prospective report.

26. A method for providing historic documentation and prospective treatment advice for a plurality of psychotherapy patients for a psychotherapy provider comprising the steps of:

automated collecting and recording of psychotherapy data for the patients, said psychotherapy data being in a plurality of categories, each of said plurality of categories including historic and prospective information;

choosing a subset of at least two categories from said plurality of categories;

storing a database comprising textual data corresponding to a plurality of possible psychotherapy data said data including prospective treatment advice;

referencing into said database by said psychotherapy data in said subset of at least two categories thereby selecting a portion of said textual data including prospective treatment advice; and combining said portion of said textual data with psychotherapy data including historic data from said means for automated collecting and recording thereby automatically generating at least one historic report and one prospective report.

27. A method for providing historic documentation and prospective treatment advice for a plurality of psychotherapy patients for a psychotherapy provider comprising the steps of:

automated collecting and recording of psychotherapy data for the patients, said psychotherapy data being in a plurality of categories, each of said plurality of categories including historic and prospective information;

choosing at least two subsets of categories from said plurality of categories;

storing a database comprising textual data corresponding to a plurality of possible psychotherapy data said data including prospective treatment advice;

referencing into said database by said psychotherapy data in said at least two subsets of categories thereby selecting a portion of said textual data including prospective treatment advice; and combining said portion of said textual data with psychotherapy data including historic data from said means for automated collecting and recording thereby automatically generating at least one historic report and one prospective report.

28. A method for providing historic documentation and prospective treatment advice for a plurality of psychotherapy patients for a psychotherapy provider comprising the steps of:

automated collecting and recording of psychotherapy data for the patients, said psychotherapy data being in a plurality of categories, each of said plurality of categories including historic and prospective information;

pseudo-randomly choosing a subset of categories from said plurality of categories;

storing a database comprising textual data corresponding to a plurality of possible psychotherapy data said data including prospective treatment advice;

referencing into said database by said psychotherapy data in said subset of categories thereby selecting a portion of said textual data including prospective treatment advice; and combining said portion of said textual data with psychotherapy data including historic data from said means for automated collecting and recording thereby automatically generating at least one historic report and one prospective report.

29. A method for providing historic documentation and prospective treatment advice for a plurality of psychotherapy patients for a psychotherapy provider comprising the steps of:

means for automated collecting and recording of psychotherapy data for the patients, said psychotherapy data being in a plurality of categories, each of said plurality of categories including historic and prospective information, said categories including emotional, physical, intellectual, social and spiritual categories;

choosing a subset of categories from said plurality of categories;

storing a database comprising textual data corresponding to a plurality of possible psychotherapy data said data including prospective treatment advice;

referencing into said database by said psychotherapy data in said subset of categories thereby selecting a portion of said textual data including prospective treatment advice; and combining said portion of said textual data with psychotherapy data including historic data from said means for automated collecting and recording thereby automatically generating at least one historic report and one prospective report.

30. The apparatus of claim 23 wherein said at least two subsets of categories includes a first subset for the generation of additional assessment data, a second subset for the generation of short term objections and a third subset for the generation of therapeutic interventions.

31. The apparatus of claim 24 wherein said processing means pseudo-randomly chooses at least two subsets of categories.

32. The apparatus of claim 25 wherein the automated collecting and recording of patient psychotherapy data and the automated generation of said at least one historical and one prospective report originates from, and is indexed to, a list of possible psychotherapeutic problems.

33. The method of claim 26 wherein said at least two categories cause said at least one historical and one prospective report to be multi-dimensional.

34. The method of claim 27 wherein said at least two subsets of categories includes a first subset for the generation of additional assessment data, a second subset for the generation of short term objections and a third subset for the generation of therapeutic interventions.

35. The method of claim 28 wherein said processing means pseudo-randomly chooses at least two subsets of categories.

36. The method of claim 29 wherein the automated collecting and recording of patient psychotherapy data and the automated generation of said at least one historical and one prospective report originates from, and is indexed to, a list of possible psychotherapeutic problems.

* * * * *